United States Patent
Chang et al.

(10) Patent No.: US 6,711,297 B1
(45) Date of Patent: Mar. 23, 2004

(54) METHODS AND APPARATUS FOR DYNAMIC TRANSFER OF IMAGE DATA

(75) Inventors: Paul Joseph Chang, Allison Park, PA (US); Carlos A. Bentancourt, Pittsburgh, PA (US)

(73) Assignee: University of Pittsburgh - of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 09/339,077

(22) Filed: Jun. 23, 1999

Related U.S. Application Data

(60) Provisional application No. 60/091,697, filed on Jul. 3, 1998.

(51) Int. Cl.[7] ................................................. G06K 9/36
(52) U.S. Cl. ........................ 382/240; 382/232; 382/233
(58) Field of Search ................................. 382/240, 233, 382/232; 709/202, 246; 250/291

(56) References Cited

U.S. PATENT DOCUMENTS

| | | | |
|---|---|---|---|
| 4,222,076 A | 9/1980 | Knowlton | 358/263 |
| 4,751,742 A | 6/1988 | Meeker | 382/41 |
| 4,853,779 A | 8/1989 | Hammer et al. | 358/133 |
| 4,943,855 A | 7/1990 | Bheda et al. | 358/133 |
| 5,097,331 A | 3/1992 | Chen et al. | 358/138 |
| 5,436,447 A | * 7/1995 | Shew | 250/291 |
| 5,539,658 A | 7/1996 | McCullough | |
| 5,548,708 A | 8/1996 | Sakashita et al. | 395/162 |
| 5,563,960 A | 10/1996 | Shapiro | 382/239 |
| 5,577,134 A | 11/1996 | Westerink | 382/240 |

(List continued on next page.)

FOREIGN PATENT DOCUMENTS

| | | | |
|---|---|---|---|
| EP | 0 701 375 A2 | 8/1994 | |
| EP | 0 669 765 A2 | 8/1995 | |
| WO | PCT/GB96/00623 | 9/1996 | H04N/1/41 |
| WO | PCT/AU97/00724 | 5/1998 | G06T/9/40 |

OTHER PUBLICATIONS

Bradley et al., "The Wavelet / Scalar Quantization Compression Standard for Digital Fingerprint Images", Proc. of IEEE International Symposium on Circuits and Systems, May 1994, vol. 3, pp. 205–208.*

Chee, Y.–Kheong, Survey of Progressive Image Transmission Methods, Imago Multimedia Centre, John Wiley & Sons, 1999.

Rogge, B., "Region of Interest Based Progressive Transmission of Greyscale Images Across The Internet", University of Ghent.

Richard L. Phillips, "A Bridge from Full–Function to Reduced–Function Workstations",I.E.E.E. Computer Graphics and Application 6, (May 1986) NY, NY.

*Primary Examiner*—Anh Hong Do
(74) *Attorney, Agent, or Firm*—Stattler Johansen & Adeli, LLP

(57) ABSTRACT

A dynamic transfer syntax efficiently transfers data, including large data images, from a server to at least one client. Source data is transformed into a hierarchical representation. The hierarchical representation, consisting of essentially non-redundant data, is a plurality of levels of transform data, such that a level of the hierarchical representation comprises transform data sufficient to reconstruct the source data at a resolution corresponding to the level. The server transfers transform data from a level of the hierarchical representation corresponding to a desired resolution. To render a new view of the source image at the client, the client requests from the server coefficients of the transform data necessary to reconstruct the new view. In response to the request, the server transfers to the client the additional transform data, and the client reconstructs the new view from the coefficients transferred. A medical imaging application for the dynamic transfer syntax is disclosed.

21 Claims, 19 Drawing Sheets

U.S. PATENT DOCUMENTS

| | | | |
|---|---|---|---|
| 5,585,852 A | 12/1996 | Agarwal | 348/398 |
| 5,600,373 A | 2/1997 | Chui et al. | 348/397 |
| 5,602,589 A | 2/1997 | Vishwanath et al. | 348/398 |
| 5,604,824 A | 2/1997 | Chui et al. | 382/248 |
| 5,619,998 A | 4/1997 | Abdel-Malek et al. | 128/660.07 |
| 5,621,660 A | 4/1997 | Chaddha et al. | 364/514 R |
| 5,703,965 A | 12/1997 | Fu et al. | 382/232 |
| 5,710,835 A * | 1/1998 | Bradley | 382/233 |
| 5,724,070 A | 3/1998 | Denninghoff et al. | 345/202 |
| 5,740,428 A | 4/1998 | Mortimore et al. | 395/615 |
| 5,742,892 A | 4/1998 | Chaddha | 455/5.1 |
| 5,764,807 A | 6/1998 | Pearlman et al. | 382/240 |
| 5,768,535 A | 6/1998 | Chaddha et al. | 395/200.77 |
| 6,012,083 A * | 1/2000 | Savitzky et al. | 709/202 |
| 6,067,383 A * | 5/2000 | Taniguchi et al. | 382/240 |
| 6,314,452 B1 | 11/2001 | Dekel et al. | 709/203 |

* cited by examiner

|   | 1K | 2K |   |
|---|---|---|---|
| | Low Low (Level 2) | Low High (Level 2) | |
| 1K | | | |
| | High Low (Level 2) | High High (Level 2) | |
| 2K | | | |

FIG. 2E

METHODS AND APPARATUS FOR DYNAMIC TRANSFER OF IMAGE DATA

CROSS-REFERENCES TO RELATED APPLICATIONS

This application claims the benefit of U.S. Provisional Application No. 60/091,697, filed Jul. 3, 1998, entitled "Flexible Representation and Interactive Image Data Delivery Protocol."

BACKGROUND OF THE INVENTION

1. Field of the Invention

The present invention is directed toward the field of data transfer, and more particularly toward efficient techniques for transferring large amounts of data over networks.

2. Art Background

Historically, imaging systems have relied upon photographic film for the storage, distribution, and use of images. For example, medical images such as X-rays historically have been rendered on film sheets. The film sheets are stored in a repository such as a medical records library, and they are retrieved and distributed to doctors or other individuals for viewing. The images are viewed by placing the film on a viewing box that passes light through the film.

However, the use of photographic film for some imaging applications has considerable drawbacks. The need to physically retrieve a film from a repository imposes undue delay, particularly problematic when access time is important, such as when a medical emergency exists. Also, films tend to get lost or misplaced, so that costs may be increased and/or the quality of services rendered may be decreased.

For these reasons and others, it has become more common for images to be stored, distributed, and viewed in digital form using computer technology. In the medical field Picture Archival and Communication Systems or PACS have been in widespread use. In a typical PACS application, image data obtained by imaging equipment such as CT scanners or MRI scanners is stored in the form of computer data files. The size of a data file for an image varies depending on the size and resolution of the image. For example, a typical image file for a diagnostic-quality chest X-ray is on the order of 10 megabytes (MB). The image data files are usually formatted in a "standard" or widely accepted format. In the medical field, one widely used image format is known as DICOM. The DICOM image data files are distributed over computer networks to specialized viewing stations capable of converting the image data to high-resolution images on a CRT display.

In imaging applications, such as medical imaging, it is important to display images at a high resolution, so that image details having potential diagnostic significance are visible. Concurrent viewing of multiple images, captured over time, is also desirable in order to enable the detection of changes that occur over a time period. The need for high resolution and multiple views translates into a need for high network bandwidth, large storage capacity, and significant processing power at the viewing stations. The traditional digitally encoded medical images, used in medical applications, usually require powerful and expensive computer systems to archive, distribute, manipulate, and display the medical images. Consequently, many current imaging systems, such as PACS, are very expensive. Because of this, a medical center having a PACS may have only a few image viewing stations, used primarily by specialists such as radiologists.

The demand for network bandwidth is very "bursty" in traditional image viewing systems, because typically the entire image is transferred to the viewing station over a brief interval after the image is requested. Significant network bandwidth is required in order to minimize the delay in rendering the image. For example, transmission of a 100 megabyte file over a network requires a large amount of bandwidth. Additional computer applications also require the transfer, over networks, of large data files. These large data files, such as medical images, present problems for servers, networks, and clients that possess limited resources. In addition to bandwidth, large processing resources, such as high-end computer workstations, are necessary to expeditiously process large data files.

With the speed of central processing units (CPUs) doubling every eighteen months, medical professionals have expected medical imaging computers to achieve the same level of improvement in price and performance. However, in reality, the input/output and transmission bandwidth of these computer systems have been less successful in making similar advances in speed and performance. For example, to transmit a sixteen bit per pixel medical image with a resolution of 512×512 pixels, approximately thirty-two seconds is required to transmit over an ISDN line at a rate of one hundred and twenty eight kilobits per second. Accordingly, it is desirable to develop techniques that efficiently transfer and manipulate large data files.

One desirable feature of some systems is the ability to allow a user to interact with the data file by selecting portions of the file to view. However, prior art techniques to transfer large data files require a user to wait an unacceptable amount of time to view the requested image. For example, it takes two seconds to receive a two kilobyte×2.5 K image (2 bytes per pixel) via a 5 megabyte per second communication link, and subsequently down sample and re-display less than twenty-five percent of the image data to a 1 K×1 K resolution display. The result of this slow downloading of data is compounded by some applications that require display of multiple images during a single session, such as medical imaging applications that require display of multiple images during evaluation. Even when employing the best lossless image data compression, which provides a three to one reduction in size, it still takes more than ten seconds to execute the transfer. These long latency periods render user interactive applications impractical. This bandwidth bottleneck is even more evident with the proliferation of Internet web applications. Also, significant resources are required at the client to manipulate the image in real time. Due to the above limitations, real-time user interaction with a system that displays large data files is prohibitive, if not impossible, using prior art techniques. Accordingly, it is desirable to develop a system that permits real-time user interaction with systems that transmit large data files over a network. It is also desirable to develop a system that balances the consumption of resources among server, network and client.

One model for transferring large data files over a network that attempts to maximize computer resources is known as the thin/thick client model. For example, the thin/thick client model for picture archive and communication system ("PACS") covers environments that include a central server or capture device with various classes of review stations at different communication bandwidths. The "thick client" typically consists of an expensive, high-resolution primary diagnosis station, and the "thin client" consists of one of numerous satellite stations with various display resolutions and communication links. The thick clients, which are rarely configured without high-resolution monitors and a high-speed communication link to the image capture device or database, typically cost over $100,000. The majority implementations for thin clients are terminals equipped with a 1280×1024 monitor and 10 baseT connection. For medical imaging applications, the thin client stations are typically not used for primary diagnoses, but are used as stations for consulting among physicians or conducting secondary diagnoses.

Typically, compression is used as the approach to solve bandwidth limited applications. Picture coding, using compression, has existed in the prior art for many decades. For example, facsimile machines, video telephones, digital video disk (DVD) players, digital satellite systems (DSSs), television receivers, and digital cameras are everyday appliances that all employ some type of image compression. However, with all the advancement in picture coding, the use of compression in medical imaging is very limited. Most of these compression schemes are lossy, in that data is lost when undergoing compression. Lossy compression is typically unacceptable in medical imaging applications. One reason that lossy compression is unacceptable in medical imaging applications is due to the potential liability from analyzing data of less than the highest informational content possible. In addition, lossy compression introduces unwanted artifacts into the medical image. Accordingly, it is imperative that medical images used in computer applications are preserved in the highest fidelity possible for diagnoses. Thus, there is an urgent need to identify solutions, beyond compression, that manipulate and display large images, such as medical images.

To reduce system bandwidth requirements without employing lossy compression techniques, picture coding using lossless techniques may be used at a limited efficiency. As discussed above, higher efficiencies can only be obtained through use of irreversible or lossy compression schemes. Typically, in designing systems, a choice at the onset is made between the use of lossy or lossless compression. The scalability from lossless to lossy compression is not offered, and there is no scalability if the picture is coded losslessly.

Another issue in transmitting large data files, such as medical images, is that the screen display is often substantially smaller than the resolution of the image itself. Typically, pictures with resolutions larger than the display size are encoded, transmitted and processed in its entirety for subsequent display or manipulation of the image. Because of the discrepancy between the image size and the user display size, the majority of the image information is discarded after processing at the recipient computer, and thus the discarded information is not displayed on the monitor. For example, medical images larger than 4K×4K, such as mammograms, must be cropped to fit into a limited screen space. Thus, even if the entire image is transmitted over a network, only a portion of the image is used in the limited screen space. The problem of discarding large amounts of information is not addressed by the current compression methods. Accordingly, it is desirable to utilize all data transmitted over a network to more efficiently use system resources.

SUMMARY OF THE INVENTION

A dynamic transfer syntax efficiently transfers data, including large data images, from a server to at least one client. Source data is transformed into a hierarchical representation. The hierarchical representation, consisting of essentially non-redundant data, is a plurality of levels of transform data, such that a level of the hierarchical representation comprises transform data sufficient to reconstruct the source data at a resolution corresponding to the level. A client application, running on the client, displays portions of the source data, including large images, to a user. For example, the dynamic transfer syntax of the present invention has applications in medical imaging. For this embodiment, the source data includes a digitized medical image generated from medical instrumentation.

To render an initial view at the client, which consists of a portion of the source image, the server transfers transform data from a level of the hierarchical representation corresponding to a desired resolution. In one embodiment, the server transfers transform data sufficient to reconstruct a low resolution view of the source image in a view finder window (e.g., 512×512 pixel window). For this embodiment, using the view finder window, the user may select specific views for display. To render a new view of the source image at the client, the client requests from the server additional transform data necessary to reconstruct the new view. Specifically, the client requests coefficients of the transform data corresponding to pixel coordinates of the new view of the source image necessary to reconstruct the source image. For example, the client may request transform data to zoom in on a particular section of the source image or to pan the source image. In response to the request, the server transfers to the client the additional transform data. The client reconstructs the new view from the coefficients transferred. Accordingly, the dynamic transfer syntax system transfers only the transform data required to reconstruct a requested image at the client, thus implementing a "just in time" data delivery system.

BRIEF DESCRIPTION OF THE DRAWINGS

FIGS. 2a–2h illustrate examples of a pyramidal data structure.

DETAILED DESCRIPTION

The disclosure of provisional application no. 60/091,697 filed Jul. 3, 1998, entitled "Flexible Representation and Interactive Image Data Delivery Protocol", is hereby incorporated by reference.

Overview of Dynamic Transfer Syntax System

Figure 1:
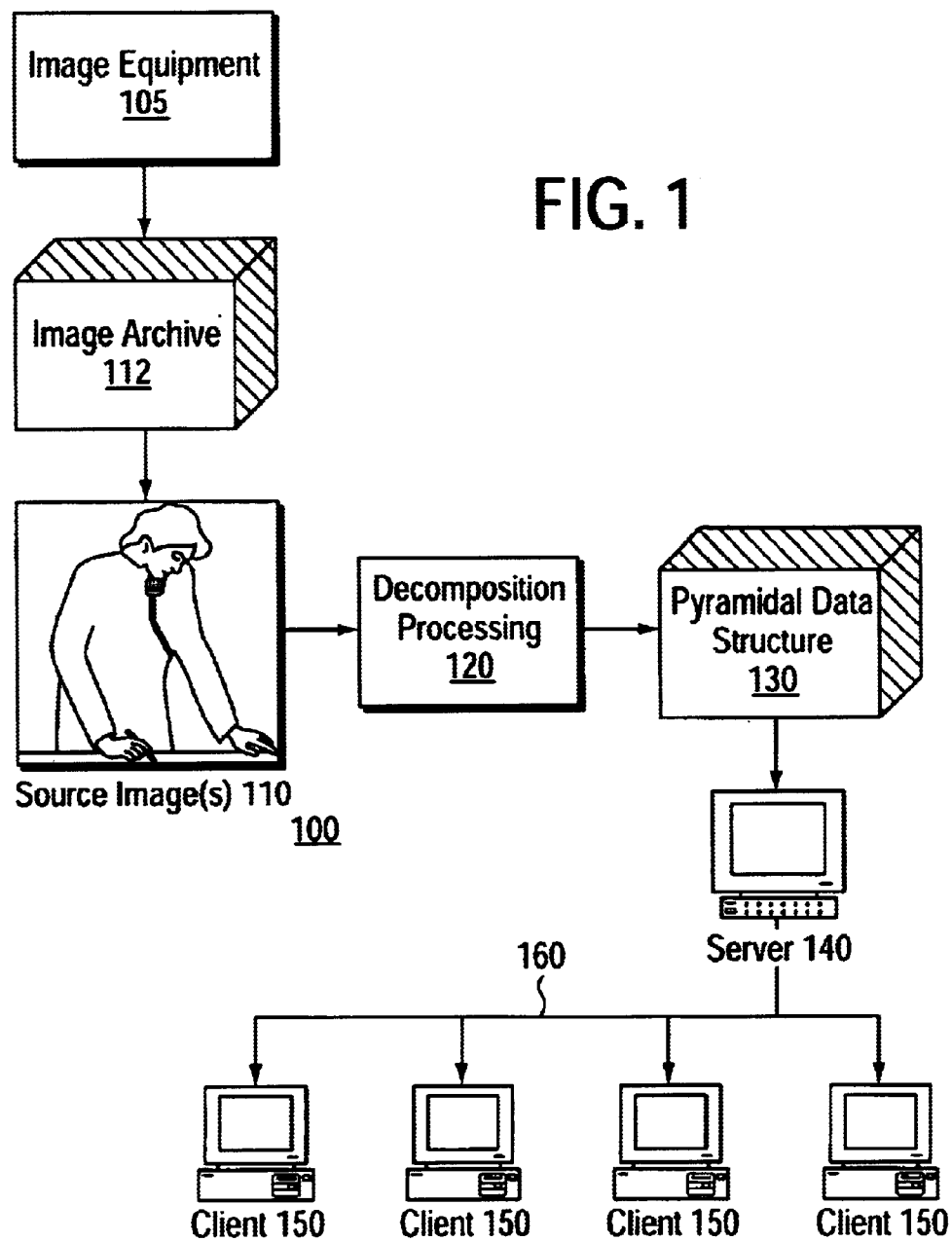
FIG. 1 illustrates one embodiment for a system that employs the dynamic transfer syntax system of the present invention.

FIG. 1 illustrates one embodiment for a system that employs the dynamic transfer syntax of the present invention. For this embodiment, a dynamic transfer syntax system 100 optionally includes imaging equipment 105 to generate source images 110 for storage in electronic form in an image archive 112. The image archive 112 contains electronic storage components such as disk drives and tape drives used to store the images in a highly reliable manner. The images are stored in a suitable archival format, such as the above-mentioned DICOM format. The imaging equipment 105 includes any type of equipment to generate images, including medical equipment (e.g., X-ray equipment, CT scanners, and MR scanners).

For this embodiment, the dynamic transfer syntax system 100 includes at least one server 140 and one or more clients, each labeled 150 on FIG. 1. The server 140 and client(s) 150 are coupled via a network 160. As shown in FIG. 1, the source image(s) 110, subsequent to decomposition processing 120, are distributed to one or more servers 140. In turn, the source image(s) 110 are available to a number of clients 150. In general, the server(s) 140 are general-purpose computers having storage and communication resources adequate to service one or clients 150. The client(s) 150 computers include, at a minimum, a graphic display and a user interface that permits zooming, panning, and other image-manipulation functions. In one embodiment, each server 140 may be associated with a particular "context" of image viewing. For example, one server 140 may be available to a radiology department, and an associated client(s) 150 may be used primarily by radiologists. Another server 140 may be used primarily for teaching or research purposes. Each context may have different requirements for image access and use, and so the use of context-specific servers can provide desirable flexibility and tailoring of the system to optimize the use of resources.

The source image 110 is processed, by decomposition processing 120, to generate a pyramidal data structure 130. For this embodiment, the server 140 transmits to client(s) 150 transformations of the source image 110, stored as pyramidal data structure 130, to re-create images and sub-images in the client(s) 150. The dynamic transfer syntax system 100 transfers only the coefficient data required to reconstruct a requested image at the client(s), thus implementing a "just in time" data delivery system. As is described more fully below, the techniques of the dynamic transfer syntax system permit use of a network 160 with moderate bandwidth capacity, while still providing low latency for transfer of large data files from server 140 to clients 150. For example, network 160 may utilize an Ethernet (10 baseT) medium or an ISDN transmission medium. Regardless, any network, including wide area networks (WANs) and local area networks (LANs) may be used with the dynamic transfer syntax system without deviating from the spirit and scope of the invention.

The dynamic transfer syntax system 100 processes one or more source images 110. Generally, the source image 110 comprises any type of a large data file, and in fact the source image 110 may comprise any type of large data file for transfer over a network environment. In one medical imaging application, the source image 110 includes a digitized medical image generated from medical instrumentation (e.g., mammogram, X-Ray, MRI, CATSCAN, etc.). Although the present invention is described for use in processing, transferring, and displaying medical images, any large data file may be used as a source image 110 without deviating from the spirit or scope of the invention.

Pyramidal Data Structure

The source image(s) 110 are input to decomposition processing 120. In general, decomposition processing 120 transforms the source images 110 into the dynamic transfer syntax representation, also referred to herein as pyramidal data structure 130. In general, the pyramidal data structure 130 comprises a hierarchical representation of the source image. Each level of the hierarchical representation is sufficient to reconstruct the source image at a given resolution. In one embodiment, the decomposition processing 120 utilizes a sub-band decomposition to generate the hierarchical representation. In general, sub-band decomposition consists of executing a process to separate "high-pass" information from "low-pass" information. For the sub-band decomposition embodiment, decomposition processing 120 comprises a finite impulse response (FIR) filter.

In one embodiment that uses sub-band decomposition, the decomposition processing 120 uses wavelet transforms, which are a sub-class of the sub-band decomposition transform. In general, the wavelet transform may be selected so that the kernels aggregate a sufficient amount of the image information into the terms or coefficients. Specifically, the information is aggregated into the "low low" component of the decomposition (See the "low low" component shown in FIGS. 2a, 2d, 2e, 2f, 2g and 2h). As described more fully below, in one embodiment, kernels of the wavelet transform are selected so as to balance the computational efficiency of the transform with optimization of the aggregate information in the low pass components. This characteristic of wavelet transforms permits transfer, and subsequent display, of a good representation of the source image at a particular resolution while maintaining the computational efficiency of the transform.

The wavelet transform function embodiment generates mathematically independent information among the levels of the hierarchical representation. Accordingly, there is no redundant information in the pyramidal data structure 130. Thus, pyramidal data structure 130 is not merely multiple replications of the source image at different resolutions, which consists of redundant information, but it contains unique data at the different levels of the hierarchical representation. As is described more fully below, the mathematically independent nature of the wavelet transform permits minimizing the amount of data transferred over a network, by requiring only the transfer of "additional data" not yet transferred to the client from the server necessary to construct a given image. The wavelet transforms are lossless, in that no data from the original source image is lost in the decomposition into the pyramidal data structure 130. Accordingly, the dynamic transfer syntax system of the present invention has applications for use in medical imaging and medical imaging applications.

In one embodiment, fixed point kernels are used in the wavelet transform (i.e., decomposition processing 120). The use of fixed point kernels generates coefficients for the pyramidal data structure that permit an easy implementation into a standard pixel footprint. The wavelet transform, a spatial transform, generates a dynamic range of the "low low" component that is equal to the dynamic range of the source image. Because of this characteristic, the "low low" component does not contain "overshoot" or Gibb's effect undershoot components. As a result, the use of fixed point kernels is preferred because no normalization process to convert the transformed dynamic range to the pixel dynamic range is required.

For this embodiment, the dynamic transfer syntax system directly utilizes the transform coefficients as pixels, without re-scaling the coefficients. The range of the high-pass components (i.e., "low high", "high low", and "high high" components) is the range of the input source data plus up to four bits per coefficient. This characteristic permits mapping of all components (i.e., high and low pass components) to a given pixel footprint. For example, source data sampled into twelve bit input samples may be stored in a sixteen bit format. For this example, each coefficient in the low-pass component (i.e., "low low" component), comprises twelve bits. The twelve bit low-pass component may be stored in the sixteen bit format. Each coefficient for the "low high" and "high low" components comprises fourteen bits (i.e., (B+2) bits per coefficient, where B is the input pixel depth per pixel), also suitable for storage in the sixteen bit format. The "high high" component consists of sixteen bits for each coefficient (i.e., (B +4) bits per coefficient, where B is the input pixel depth per pixel). Thus, the "high high" coefficients may also be stored in the sixteen bit format.

The use of the wavelet transform to generate the pyramidal data structure provides a scalable solution for transferring different portions of a large data file. When the source image 110 is decomposed into the pyramidal data structure 130, sub-images and sub-resolution images are extracted directly from memory of the server 140. The server 140 then transmits only the data, in the form of physical coefficients, required to reconstruct the exact size of the desired image for display at the client. Accordingly, the multi-resolution format is implicit in the pyramidal data structure.

The information in the pyramidal data structure is essentially non-redundant. Each level of the pyramidal data structure comprises information sufficient to reconstruct the source image at a resolution corresponding to that level. However, the different levels of the pyramidal data structure are not merely replications of the source image at different resolutions. Instead, each level of the pyramidal data structure comprises a unique set of coefficients.

A wavelet transform is a spatial transform. In general, in a spatial transform, the information is aggregated so as to preserve the predictability of the geometry of the source image. For example, using a wavelet transform with fixed point kernels, specific coefficients of the transform data may be identified that contribute to specific geometric features of the source image (i.e., a pre-defined portion of a source image is directly identifiable in the transform data). In contrast, a spectral transform aggregates the information of the source image across a frequency spectrum, and thus does not preserve the ability to predict the geometry of the original source image from the transform data.

In another embodiment, the wavelet transforms use floating point kernels. The use of floating point kernels generates an aggregated higher percentage of information in the "low low" component of the pyramidal data structure. However, in implementation, the use of floating point kernels has several disadvantages over the use of fixed point kernels. For example, use of the floating point kernels requires normalization of the coefficients to convert the coefficients in the pyramidal data structure 130 to pixel data for display at the client.

In another embodiment, the wavelet transform of the present invention may used to generate multi-spectral transform data. In general, multi-spectral transform data aggregates multi-components of the source image into a vector for the transform data. Through use of multi-spectral transform data, the wavelet transform may aggregate multi-dimensional data (e.g., two dimensional, three dimensional, etc.) for a source image. For example, multi-dimensional transform data may be used to reconstruct a source image in three dimensions. Also, the multi-spectral transform data may comprise any type of attribute for binding to the source image, such as color variations and/or non-visual components (e.g., infrared components).

In general, to generate the pyramidal data structure 130, the transform is applied across the columns, and then this transform, or a different transform, is applied across the rows. The selection of the transform for decomposition processing 120 is dependent upon the particular characteristics of the pyramidal data structure desired. Each level of the pyramidal data structure is generated by recurring on the low-pass, "low low", of the previous higher level. This recursion continues until a predetermined size is obtained. For example, in one embodiment, the lowest level in the pyramidal data structure for a source image having an aspect ratio of one-to-one consists of a low-pass component of 128×128. However, any granularity of resolution may be generated for use in a pyramidal data structure without deviating from the spirit or scope of the invention. Also, any quadrant may be used in the recursion process with any desired transform.

Figure 2A:
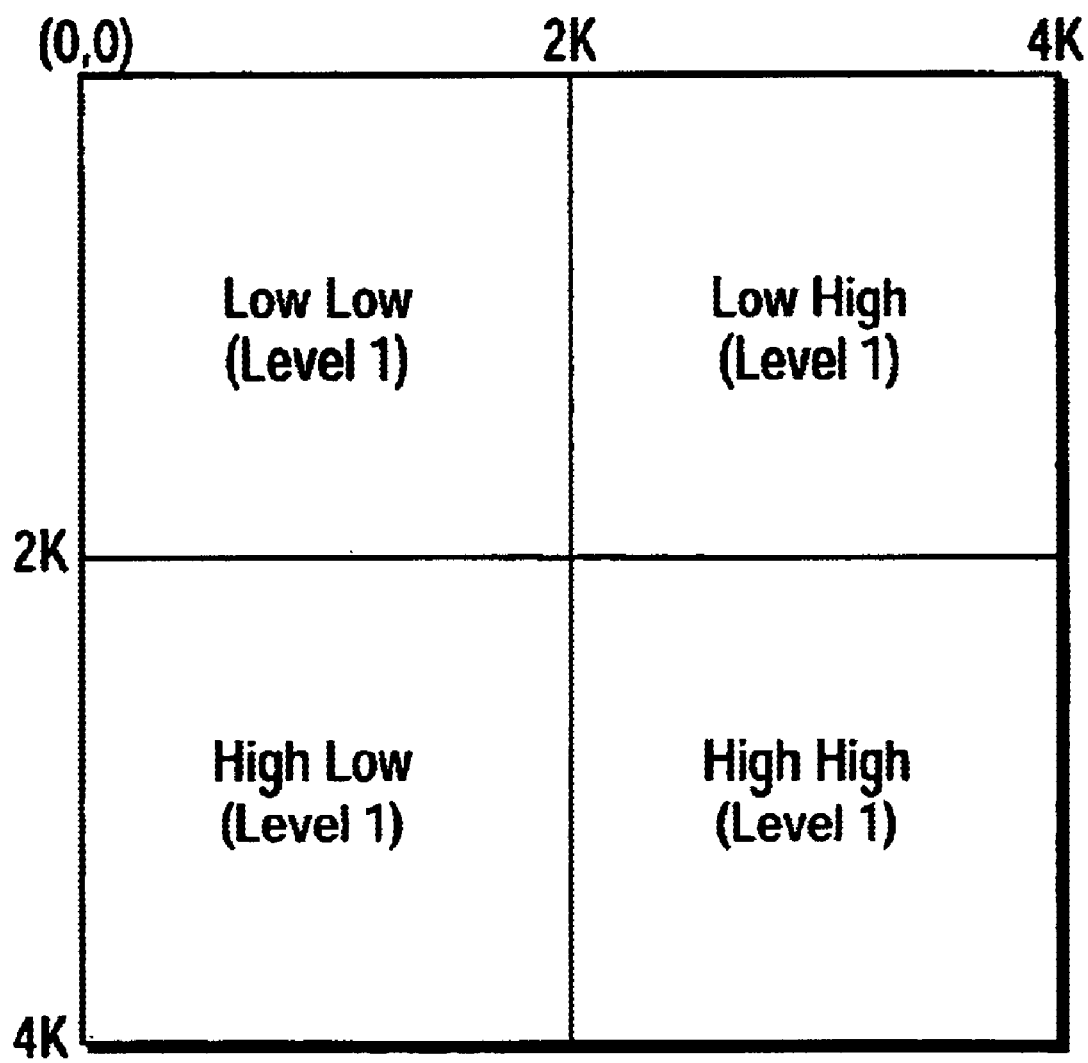
Figure 2B:
Figure 2C:
Figure 2D:
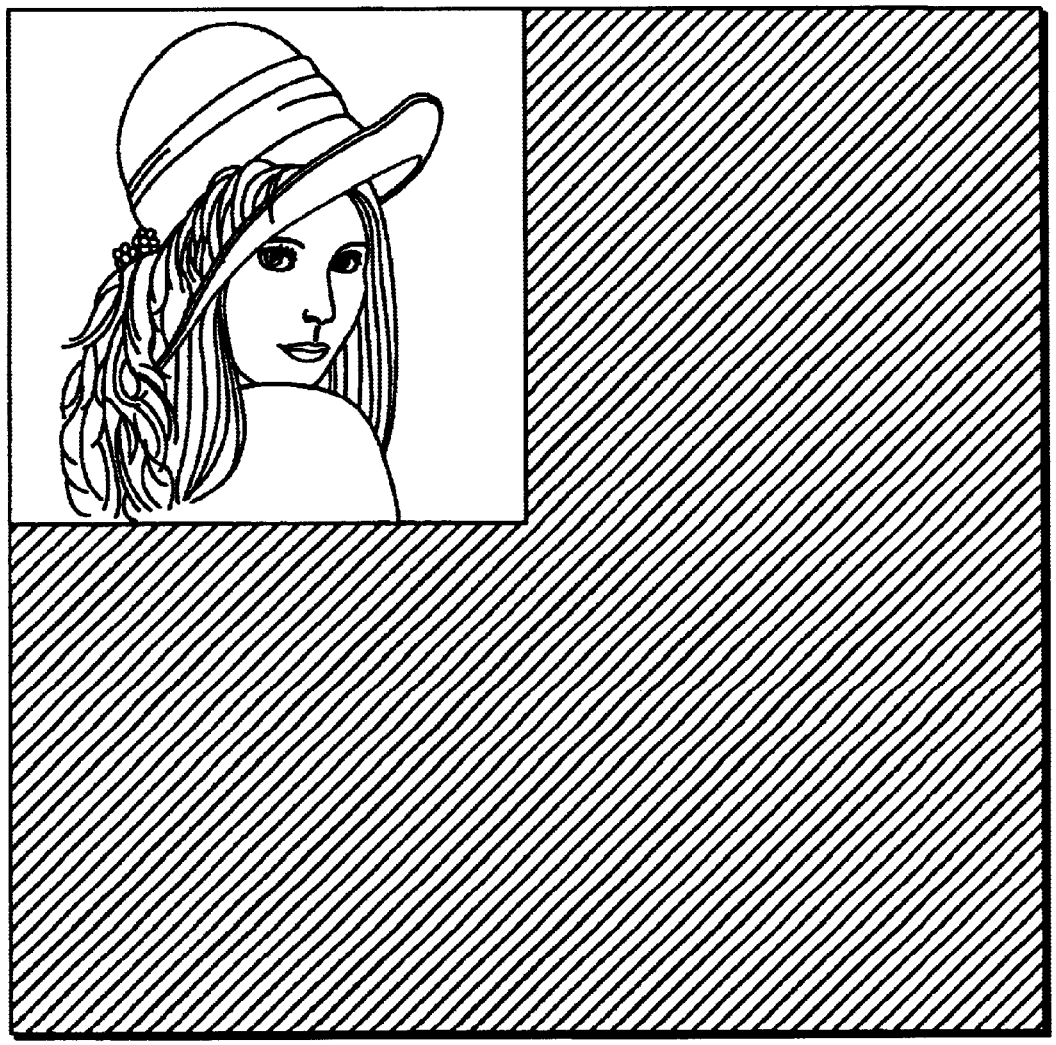

FIGS. 2a–2h illustrate examples of a pyramidal data structure. For this example, the source image comprises a 4K×4K image. The decomposition processing 120 generates, in a first iteration, a level one Mallat structure shown in FIG. 2a. Specifically, as shown in FIG. 2a, a low-pass component, "low low", is generated and consists of a 2K×2K sub-image. The high-pass components, consisting of "low high", "high high", and "high low", contain physical coefficient coordinates as shown in FIG. 2a (e.g., the upper right hand coordinate for the rectangle that constitutes the "low high" component is (4K, 0)). FIG. 2b illustrates an example source image to illustrate one embodiment for decomposition processing. FIG. 2c illustrates a level one Mallat transform of the columns of the source image shown in FIG. 2b. FIG. 2d illustrates a level one Mallat transform of the columns and rows of the source image shown in FIG. 2b.

Figure 2F:
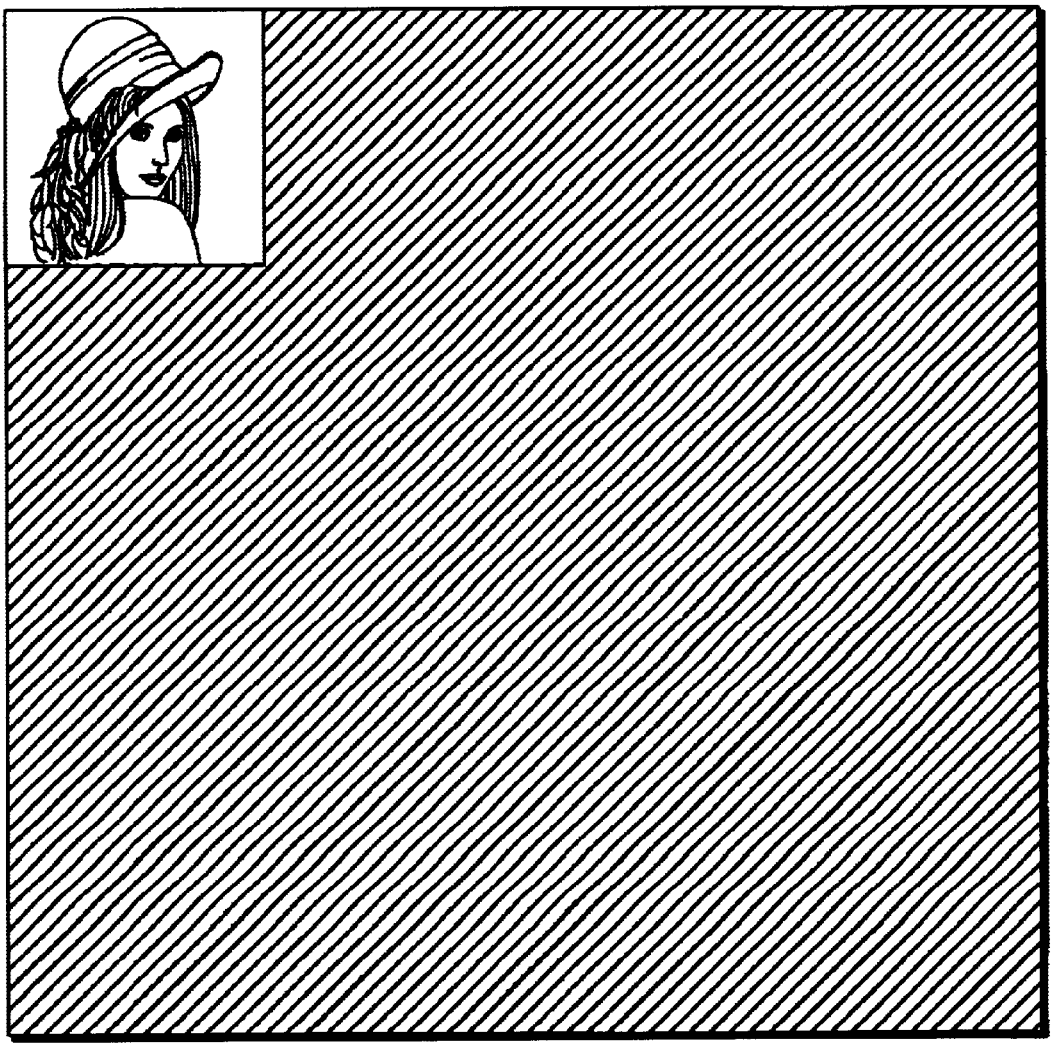
Figure 2G:
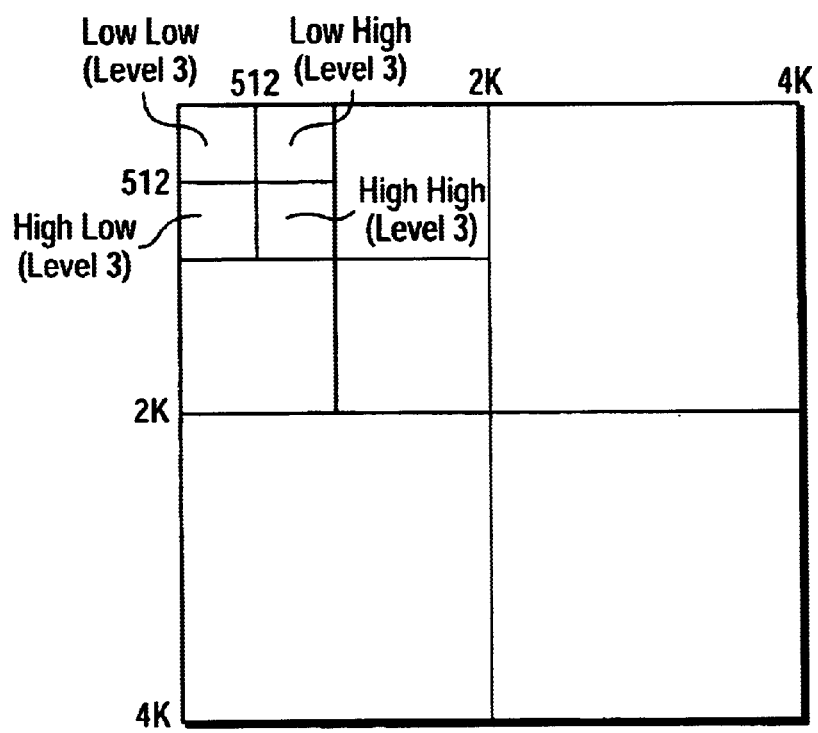
Figure 2H:
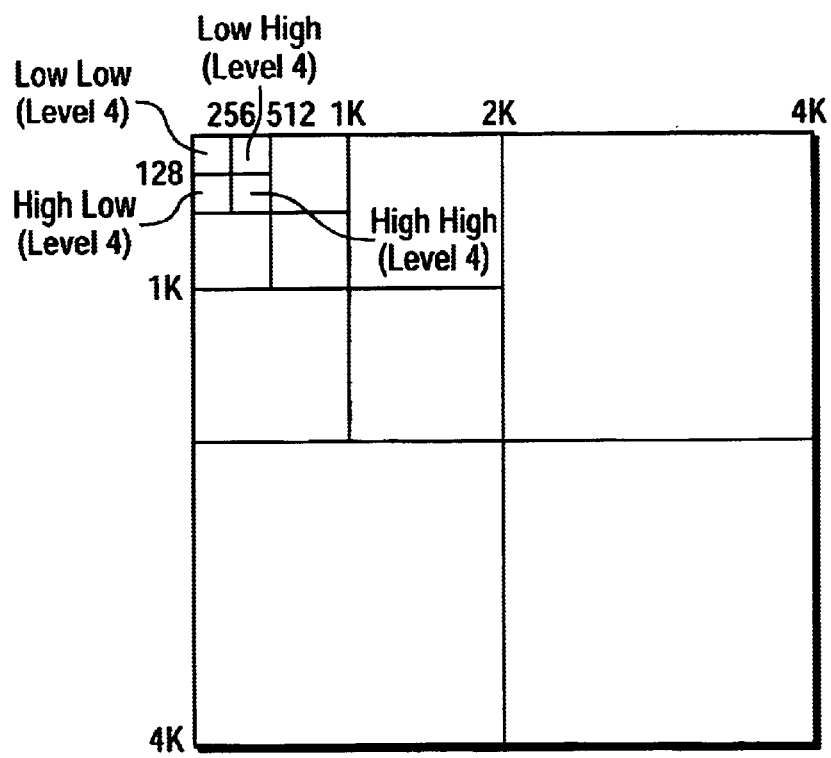

FIG. 2e illustrates a second level decomposition for the example of FIG. 2a. As shown in FIG. 2e, the second iteration of decomposition processing 120 operates on the low pass (i.e., "low low"), component of the level one data. For the second level, the low-pass component, "low low", consists of a 1K×1K sub-image. FIG. 2f illustrates a level two Mallat transform for the source image shown in FIG. 2d. FIG. 2g illustrates a level three decomposition for the examples of FIGS. 2a and 2e. To generate the level three decomposition, decomposition processing 120 operates on the level two "low low" component of FIG. 2e (i.e., the 2K×2K image). For the level three transform, the low-pass component, "low low", is a 512×512 sub-image. FIG. 2h illustrates a fourth level of decomposition for the example of FIG. 2g. For the level four transform, the low-pass component comprises a sub-image of 256×256 pixels.

In one embodiment, the wavelet kernel comprises the wavelet kernel in the Ricoh Crew Image Compression Standard proposal and is derived from D. LeGall and A. Tabatabai, See "Sub-band coding of digital images using symmetric short kernel filters and arithmetic coding techniques," IEEE International Conference on Acoustics, Speech and Signal Processing, New York, N.Y., pp. 761–765, 1988. Any sub-band kernel or pyramid transform could be used within the infrastructure described by DTS; however, an integer kernel with no coefficient growth in the low pass term has particular advantages in that the low pass coefficients can be used without processing as pixels, and the transform can be inverted exactly in the integer domain. Although floating point kernels can have superior signal transfer characteristics, the additional processing required to use these coefficients as pixels, and the need for additional storage to guarantee perfect reconstruction works to their disadvantage.

The kernel consists of a low pass and a high pass biorthogonal filter. With input defined as $\{d_j\}$ and $[x]$ defined as the floor function, the forward transform is:

$$\text{Low}[j] = [(d_{2j} + d_{2j+1})/2]$$

$$\text{High}[2] = d_{2j} - d_{2j+1} + \text{Poly}[j]$$

$$\text{Poly}[j] = [(3*\text{Low}[j-2] - 22*\text{Low}[j-1] + 22*\text{Low}[j+1] - 3*\text{Low}[j+2] + 32)/64]$$

The inverse transform, used to reconstruct the image, is:

$$d_{2j} = \text{Low}[j] + [(\text{High}[j] - \text{Poly}[j]+1)/2]$$

$$d_{2j+1} = \text{Low}[j] - [(\text{High}[j] - \text{Poly}[j])/2]$$

Dynamic Transfer Syntax Session

Figure 3:
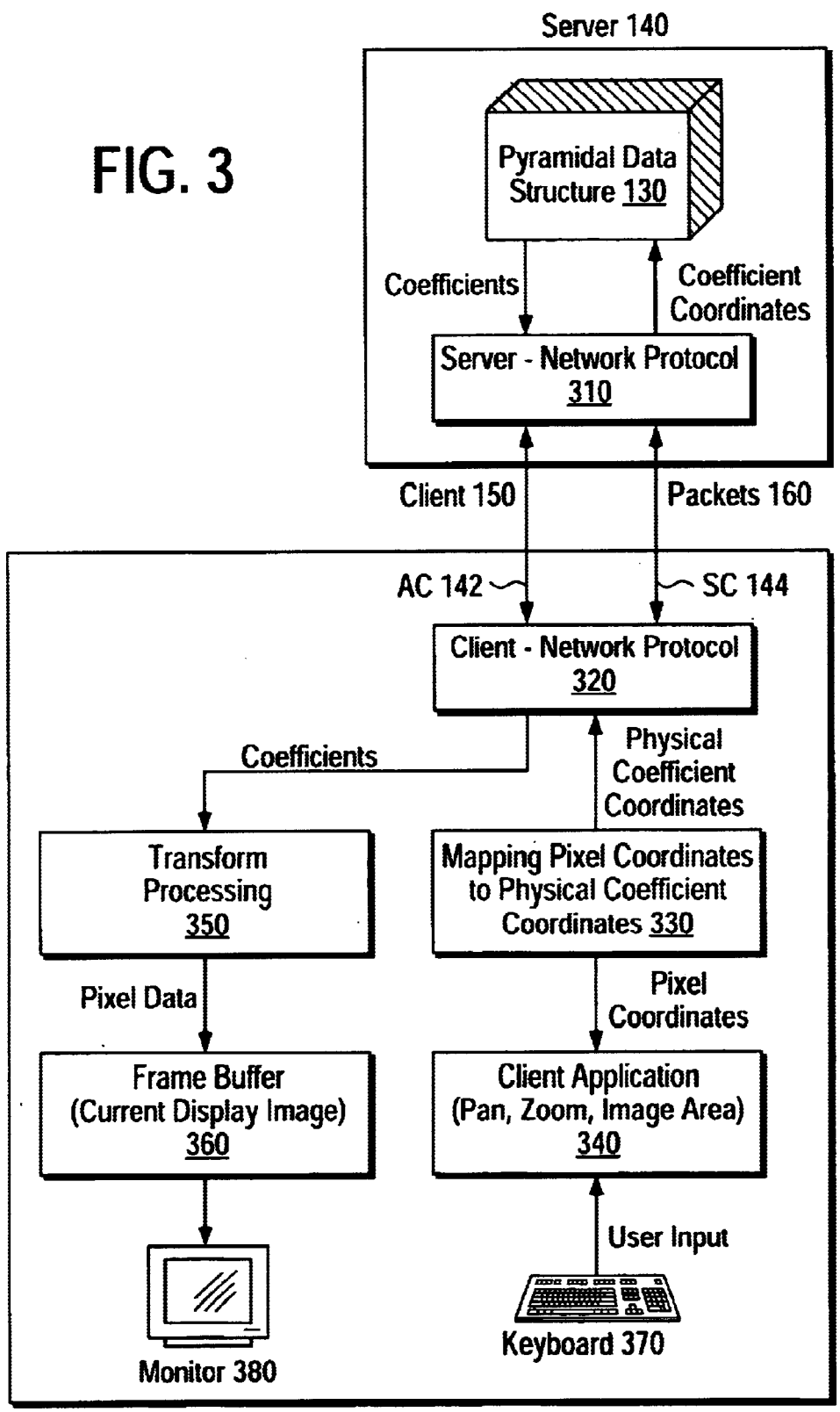
FIG. 3 is a block diagram illustrating one embodiment for the dynamic transfer syntax system of the present invention.

FIG. 3 is a block diagram illustrating one embodiment for the dynamic transfer syntax system of the present invention. This embodiment illustrates a server, storing a pyramidal data structure 130, and a client running a client application. In general, the client application 340 may comprise any type of application that permits a user to view or manipulate data downloaded from a server. In one embodiment, client application 340 is software running on a general purpose computer that permits a user to view medical images downloaded from the server 140. As shown in FIG. 3, packets are transferred across the network 160 to effectuate communication between the server 140 and a client 150. The server 130 contains server-network protocol 310, and the client contains client-network protocol 320. As described more fully below, these modules implement a network protocol to transmit the packets across network 160.

The client application 340 receives user input from an input control device, such as keyboard 370 and a cursor control device. For example, the user input may generally define selection by a user to pan or zoom on an image. In turn, the client application 340 generates the pixel coordinates, with reference to the original source image, to define the image area and the resolution of the source image selected by the user. For example, if the user desires to zoom in on a particular portion of the source image, then the client application 340 specifies the pixel coordinates that define the area of the image and the zoom factor desired. Mapping 330 receives the pixel coordinates, and generates physical coefficient coordinates that map to the pixel coordinates. The physical coefficient coordinates define the range of coefficients, stored as the pyramidal data structure, necessary to re-construct the image defined by the pixel coordinates. One embodiment for mapping pixel coordinates to physical coefficient coordinates is described more fully below in conjunction with FIG. 4. These physical coefficient coordinates are then transferred, as a request, from the client 150 to the server 140.

In response to the client request, the server 140 receives the coefficient coordinates, and transmits, over the network 160, the coefficients identified by the coefficient coordinates. This data flow is indicated by the arrows in FIG. 3. The client 150 receives the coefficients, and processes the coefficients in transform processing 350. Transform processing 350 is the reverse transform used in decomposition processing 120 (FIG. 1). The pixel data is input to a frame buffer 360 of the general purpose computer system, for subsequent display on the monitor 380.

In one embodiment, two distinct types of interfaces exist between the server 140 and a client 150. One interface is referred to as an "asynchronous channel" or AC 142. The AC 142 interconnects the server network protocol manager 310 with a master client process (not shown) located in the client 150. The other interface is referred to as a "synchronous channel" or SC 144. The SC 144 interconnects the server network protocol manager 310 with the transform processing 350 located in the client 150. The AC 142 is used primarily for the signaling of requests and responses between a client 150 and a server 140. One primary function carried out via the AC 142 is the establishment of SCs 144. The SCs 144 are used primarily for the delivery of image data. The AC 142 employs communications messages using "key value pair" syntax to provide flexibility and tailorability. Each message includes a number of text strings of the form "variable =value", where "variable" is a string identifying some aspect of the message, and "value" is a string identifying a particular value for this attribute. Examples of the use of key value pairs in AC messages are given below.

The SC 144 is tailored for the expedient request and delivery of image data between the server network protocol manager 310 and the client network protocol manager 320. The communications protocol via the SC 144 employs as little overhead as possible in order to speed message processing. This feature enables the tailoring of data request and delivery messages to enhance efficiency and/or performance.

The coefficients are requested from the client 150 in blocks. In one embodiment, each block is specified by an upper left vertex and a lower right vertex. The maximum block size for a request depends on the maximum input/output buffer size implemented on the SC 144. This buffer size is a function of the underlying network transport mechanism. For each set of coefficients being requested, the server 140 breaks the coefficients down into a number of blocks of this size or smaller, and then requests the blocks individually by specifying their respective vertices in respective block request messages. The protocol of the SC 44, therefore, is a very simple protocol that handles requests for blocks of data and the delivery of the data blocks. Messages are very easy to format and decode, and therefore the SC 44 can be operated in a fast and efficient manner.

After mapping pixel coordinates to physical coefficient coordinates (block 330), client network protocol manager 310 breaks the coefficient request into network friendly block requests. For this embodiment, the block request is composed of 7 short parameters that describe the exact location of the desired coefficient block as follows:

| | |
|---|---|
| Short[0] = 1 | used to test byte swap |
| Short[1] = 0 | Raw Request Command |
| Short[2] = X0 | Start Xdim |
| Short[3] = Y0 | Start Ydim |
| Short[4] = X1 | End Xdim |
| Short[5] = Y1 | End Ydim |
| Short[6] = Slice | Slice number |

The server network protocol manager 310 gathers information and returns a one dimensional array of short parameters where the number of elements in the array is (X1−X0)* (Y1−Y0).

The operational flow described in FIG. 3 illustrates the "just in time" data delivery of the dynamic transfer syntax system 100. Specifically, note that only the incremental coefficients necessary to re-construct the requested image is transferred from the server 140 to the client 150. This process eliminates unnecessary transfer of data that is not displayed on the monitor 380.

Figure 4:
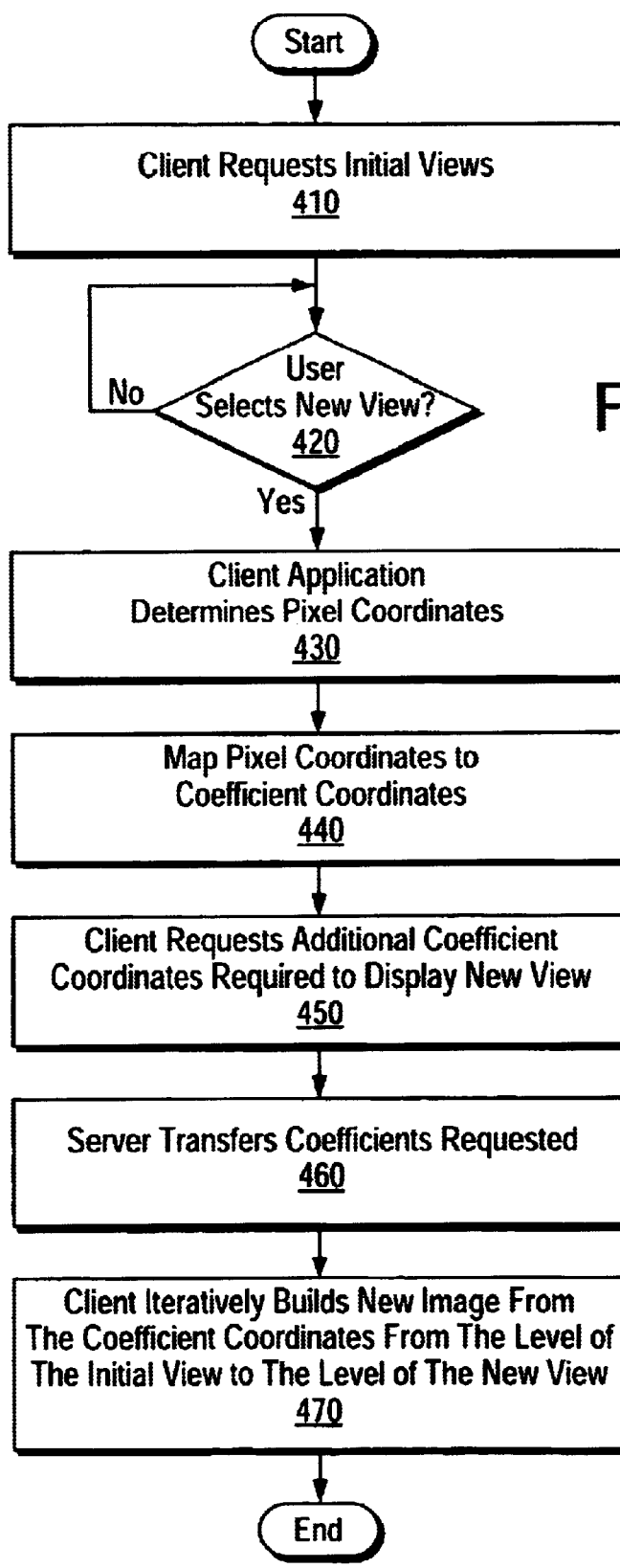
FIG. 4 is a flow diagram illustrating one embodiment for the dynamic transfer syntax system of the present invention.

FIG. 4 is a flow diagram illustrating one embodiment for the dynamic transfer syntax system of the present invention. For this embodiment, to initiate transfer of data from the server to the client, the server transfers an initial view to the client in response to a request from the server (block 410, FIG. 4). In one embodiment, the initial view is displayed in a small screen area (e.g., 512×512 rendition of the source image). One embodiment for initially displaying the source image in a reference window is described in conjunction with FIG. a. The client application (block 340, FIG. 3) permits a user to select a new view of the source image. For example, the user may select a new view by selecting an image area to increase the magnitude of the resolution for the new view (i.e., zoom in on a particular area of the source image). Regardless of the technique, if a user selects a new view, then the client application determines the pixel coordinates of the new view (blocks 420 and 430, FIG. 4). The pixel coordinates define, relative to the source image, the image area and resolution for the new view. The pixel coordinates, for the new view, are then mapped to coefficient coordinates to identify coefficients in the pyramidal data structure (block 440, FIG. 4).

In one embodiment, the decomposition processing 120 (FIG. 1) uses the wavelet transform. There is a one-to-one correspondence between pixel coordinates and coefficient coordinates, and thus no re-scaling is required. The following example illustrates mapping from pixel coordinates to physical coefficient coordinates. For purposes of nomenclature, the coordinates define a rectangle of coefficients, such that the first coordinate $[x_1, y_1]$ represents the upper left coordinate of the rectangle, and the second coordinate, $[x_2, y_2]$, represents the lower right hand corner of the rectangle. The relative sizes and locations of the coefficients are the same with respect to the size and location the original image. Thus, the indices of the coefficients at any level can be derived from the coordinates $[x_1, y_1]$ and $[x_2, y_2]$ by shifting (to account for the relative position of a rectangle of coefficients at a given level) and scaling (to account for the relative size of the rectangle of coefficients).

For this example, the initial view is displayed in the entire area of the source image in a 512×512 reference window. Thus, the transform processing 350 (FIG. 3) includes the coefficients at the coordinates:

$ti$ 3[0,0][4K, 4K]

This example assumes a 4K×4K source image. The "3" represents that the initial image, 512×512 in size, requires level "3" coefficients to render. For this example, the client application selects, for the initial view, dead center at the pixel coordinates of [1K, 1K] [3K, 3K]. This requires coefficient coordinates of:

2[1K, 1K] [3K, 3K]

After defining the physical coefficient coordinates required for the new view, the client application requests the additional coefficient coordinates required to display the new view (block 450, FIG. 4). For the example discussed above, the client requests "2 [1K, 1K][3K, 3K]" to represent the additional physical coefficients coordinates needed to display the new view. The physical coefficient coordinates are transferred over the network to the server, and in response, the server transfers the coefficients identified by the coefficient coordinates (block 460, FIG. 4). After receiving the coefficients, the client iteratively builds the new image from the coefficient coordinates from each level, starting with the initial view, to the level of pyramidal data coefficients required to display the new view (block 470, FIG. 4).

Figure 5A:
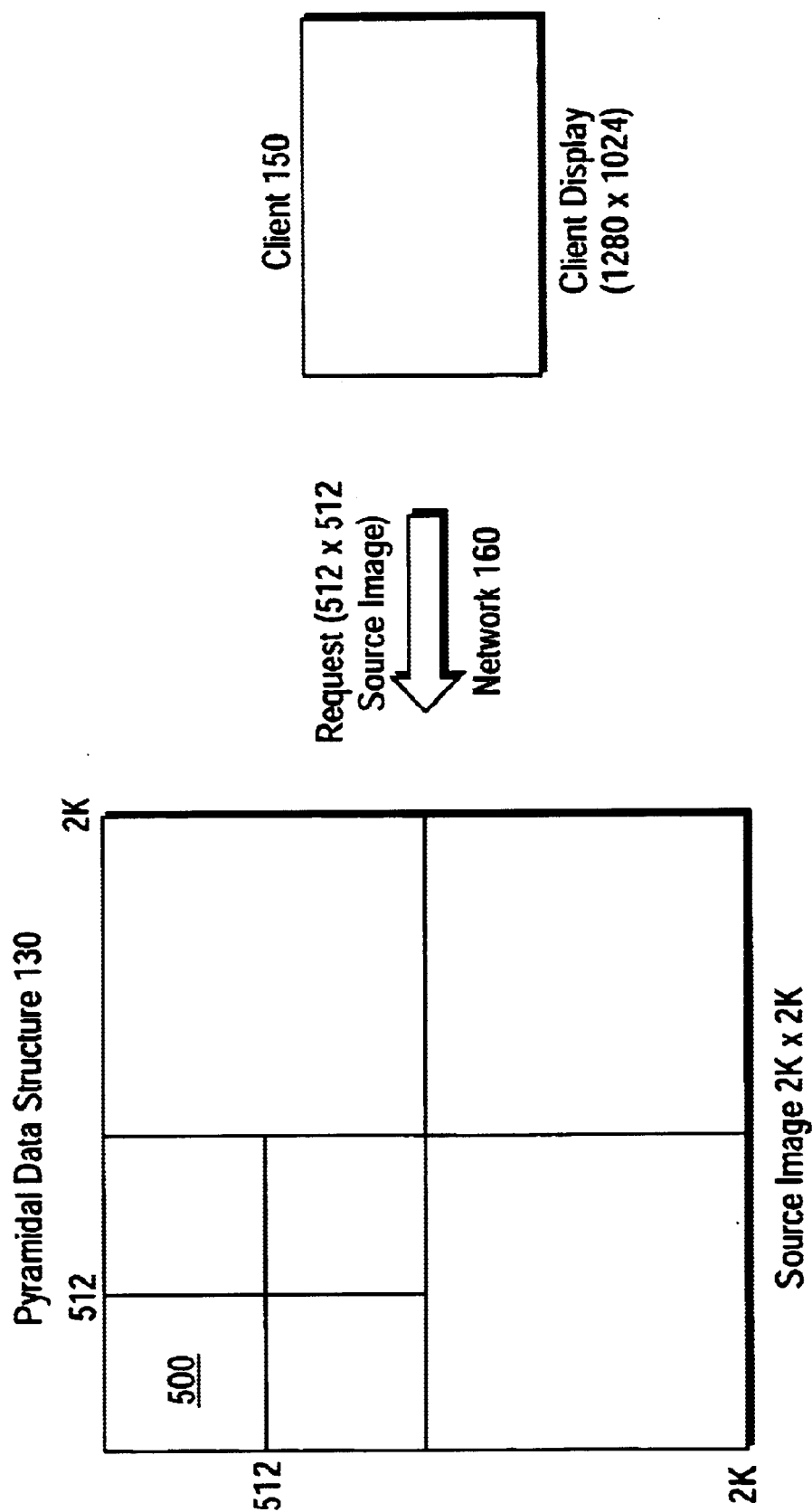
FIGS. 5a and 5b illustrate a request/transfer operation between a client and server utilizing the dynamic transfer syntax system of the present invention.
Figure 5B:
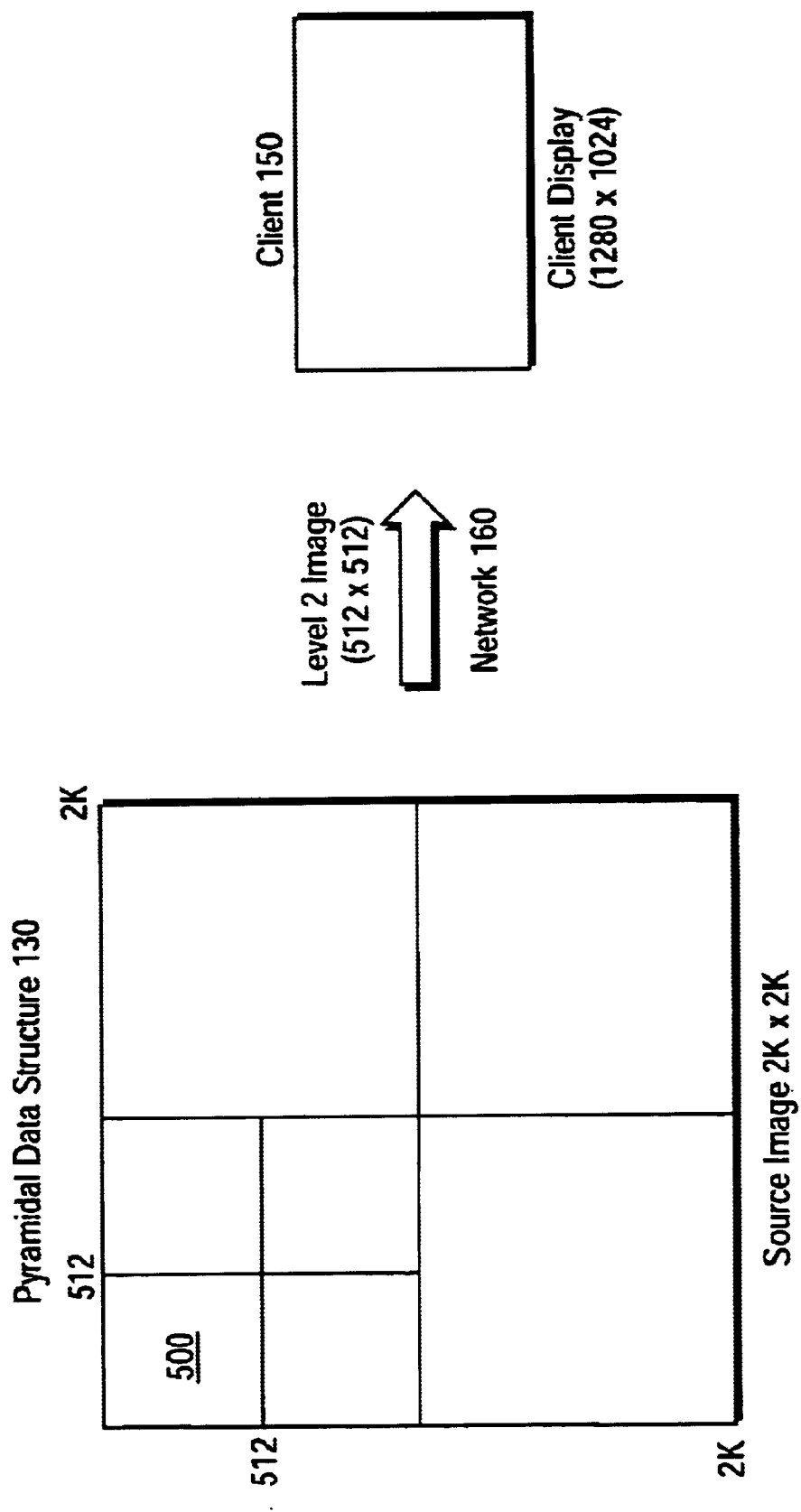

FIGS. 5a and 5b illustrate a request/transfer operation between a client and a server utilizing the dynamic transfer syntax system of the present invention. This example, the client display size is 1280×1024 pixels, and the source image is 2K×2K. To initiate the process, the client requests a 512×512 resolution of the source image as shown in FIG. 5a. For this example, a 512×512 sub-image constitutes a second level sub-image in the pyramidal data structure. In response to the request, the server transmits the low-pass component for the level three decomposition. This "low low" sub-image is highlighted on the source image in FIG. 5a. FIG. 5b illustrates the display of the 512×512 low-pass sub-image on the client display. As discussed above, for the initial window size of 512×512, the low-pass component is the best representation of the source image that can be displayed in a 512×512 window.

Figure 6A:
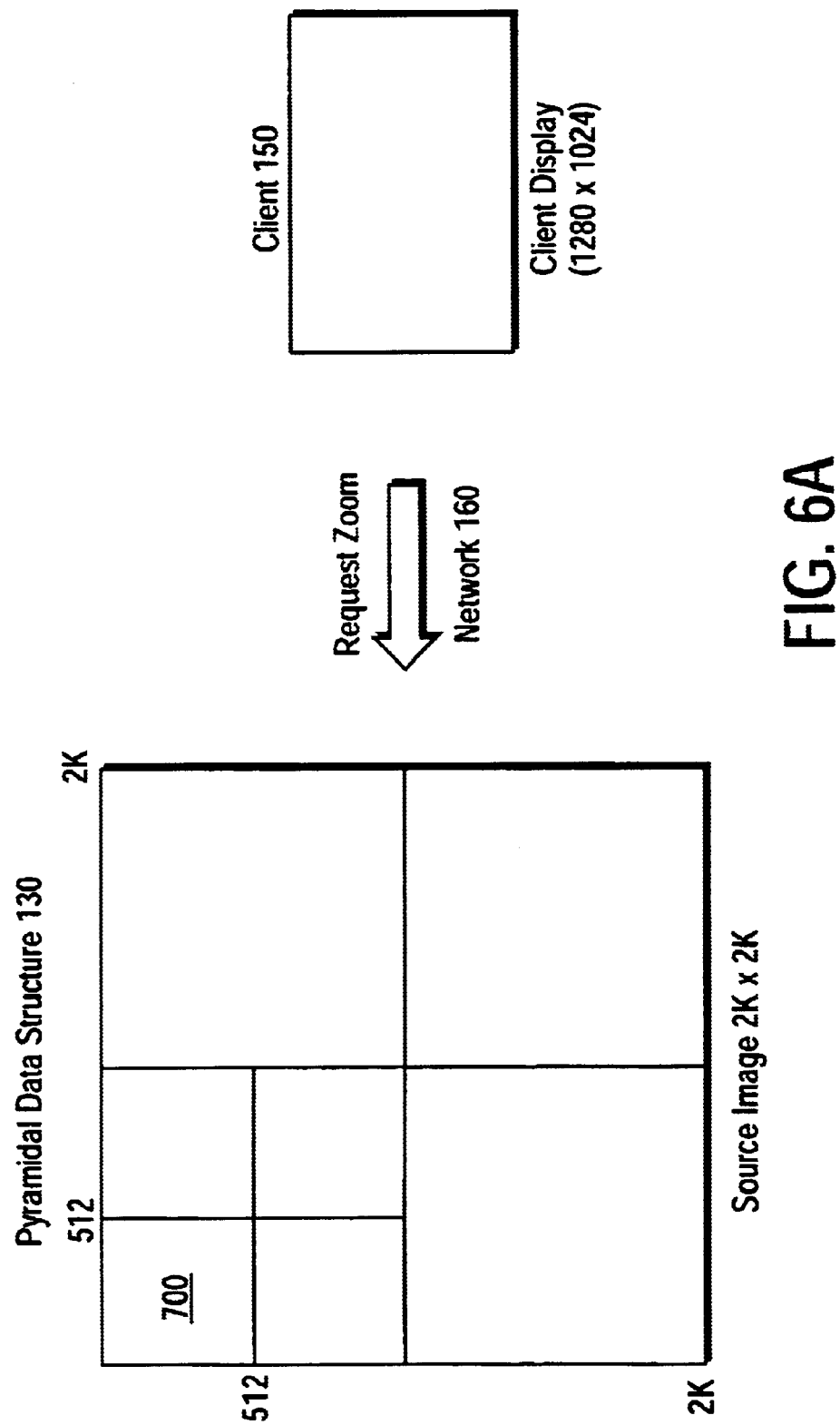
FIGS. 6a & 6b illustrate one embodiment for implementing a zoom operation for the dynamic transfer syntax system of the present invention.
Figure 6B:
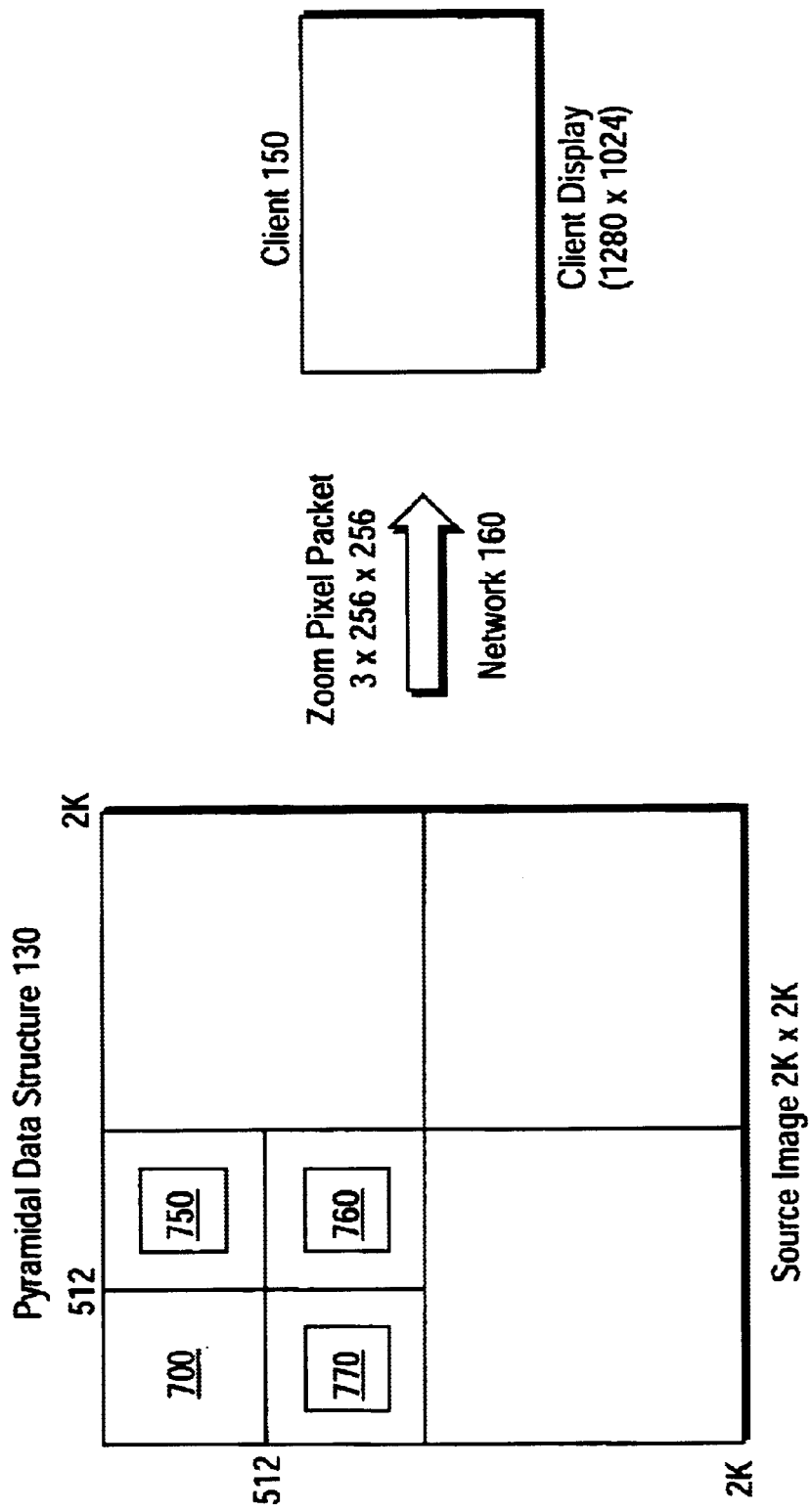

FIGS. 6a & 6b illustrate one embodiment for implementing a zoom operation for the dynamic transfer syntax of the present invention. As shown in FIG. 6a, as an initial view, the client displays, in a 1280×1024 window, a 512×512 image. The 512×512 image, a level two decomposition for a 2K×2K source image, consists of the entire source image in the smaller display window. The client requests additional coefficient coordinates sufficient to display a portion of the source image at a higher resolution (i.e., physical coordinates to execute the zoom operation). As shown in FIG. 6b, in response to the request, the server transmits three packets of coefficients, each consisting of 256×256 coefficients, to display the new view at the higher resolution. Note that the high-pass coordinates transferred provide the additional information necessary to generate the new image. The boxes labeled 750, 760 and 770 depict the high-pass coefficients necessary to generate the new image at the higher resolution.

Figure 7A:
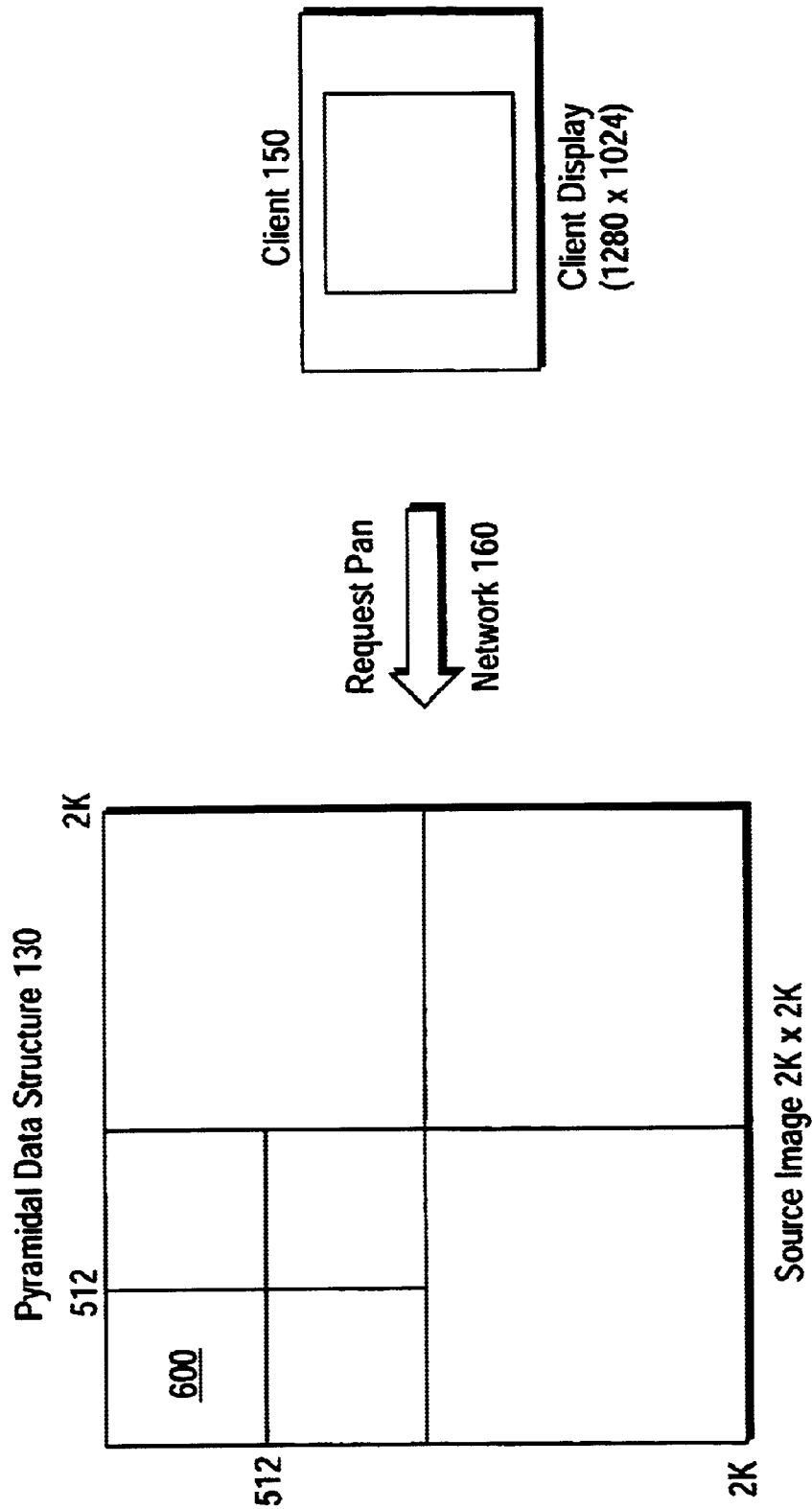
FIGS. 7a & 7b illustrate one embodiment for performing a pan operation, after execution of the zoom operation of FIGS. 6a and 6b, utilizing the dynamic transfer syntax of the present invention.
Figure 7B:
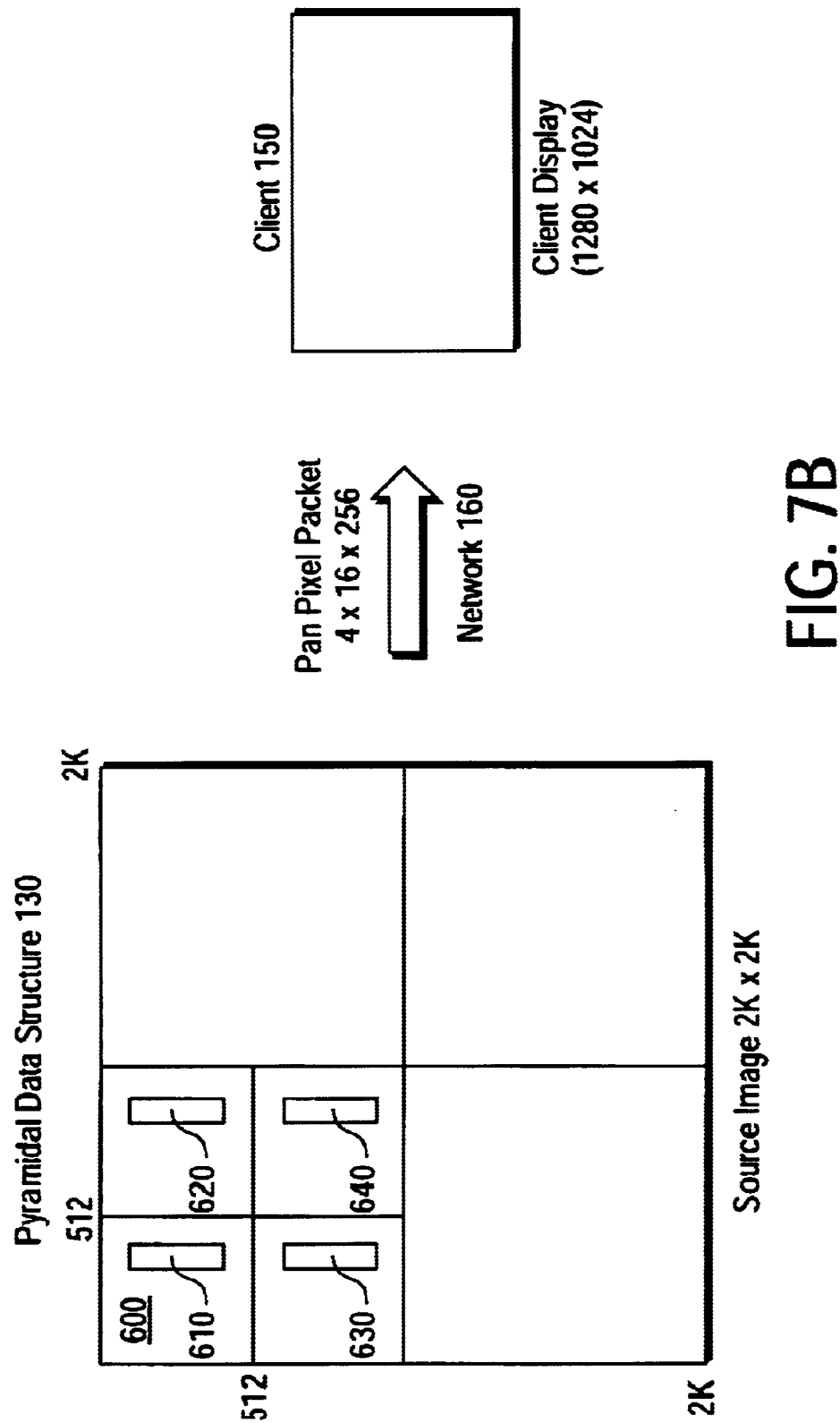

In one embodiment, the client application supports the panning of the source image. In general, panning consists of viewing, in virtual real-time, portions of the larger source image on the smaller client display. One embodiment for implementing panning in a medical imaging application is described below in conjunction with FIGS. 8a & 8b. FIGS. 7a & 7b illustrate one embodiment for performing a pan operation utilizing the dynamic transfer syntax of the present invention. The pan operation example of FIGS. 7a and 7b occurs after execution of the zoom operation illustrated in FIGS. 6a and 6b. As shown in FIG. 7a, the client displays, in a portion of the 1280×1024 display, an initial image. The initial image is a portion of the entire source image at a resolution greater than the resolution required to display the entire source image on the client display. For example, the initial image may comprise approximately one half of the source image at full scale (e.g., a 1024×1024 image consisting of the top half of the 2k×2k source image). To view a different portion of the source image (i.e., pan the source image) after the zoom operation of FIGS. 6a and 6b has been executed, the client requests a pan operation by transmitting the physical coefficient coordinates necessary to generate the new view (i.e., the portion of the zoomed source image being panned). For the example of FIGS. 7a & 7b, to pan a portion of the source image, four packets of coefficients, each consisting of 16×256, are transmitted from the server to the client via the network. The additional coefficients required for the example pan operation are graphically illustrated as boxes 610, 620, 630 and 640. As a result, the client processes the coefficients to generate the pixel data for the pan operation for display on the client display.

The foregoing description of the dynamic transfer syntax assumes that previously-requested coefficients are retained in a cache or other memory while the image is being viewed, and can be retrieved from the memory as necessary for decoding regions of the image. It may be desirable in alternative embodiments to forego such a memory, for example to reduce cost. In such memory-less embodiments, the client 150 requests all the coefficients necessary to decode a desired region, whether or not they had been previously requested.

Medical Imaging Applications

Figure 8A:
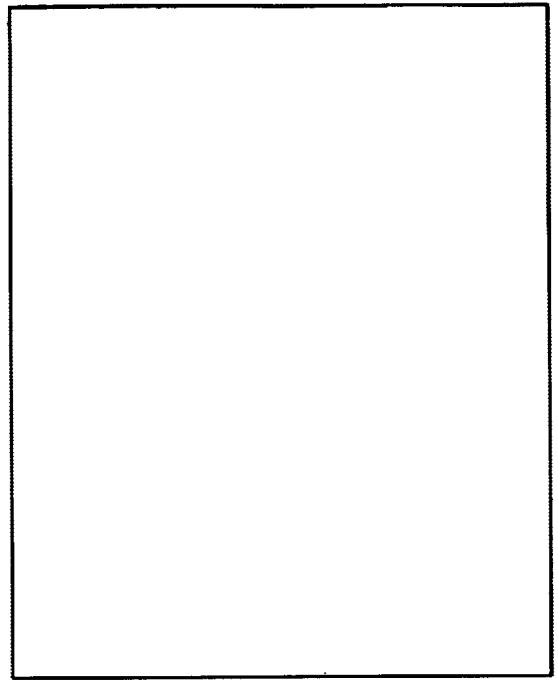
FIGS. 8a & 8b illustrate one embodiment of a client output display for implementing a medical imaging application using the dynamic transfer syntax of the present invention.
Figure 8A:
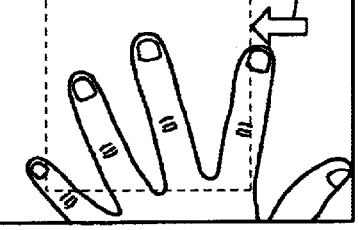
Figure 8B:
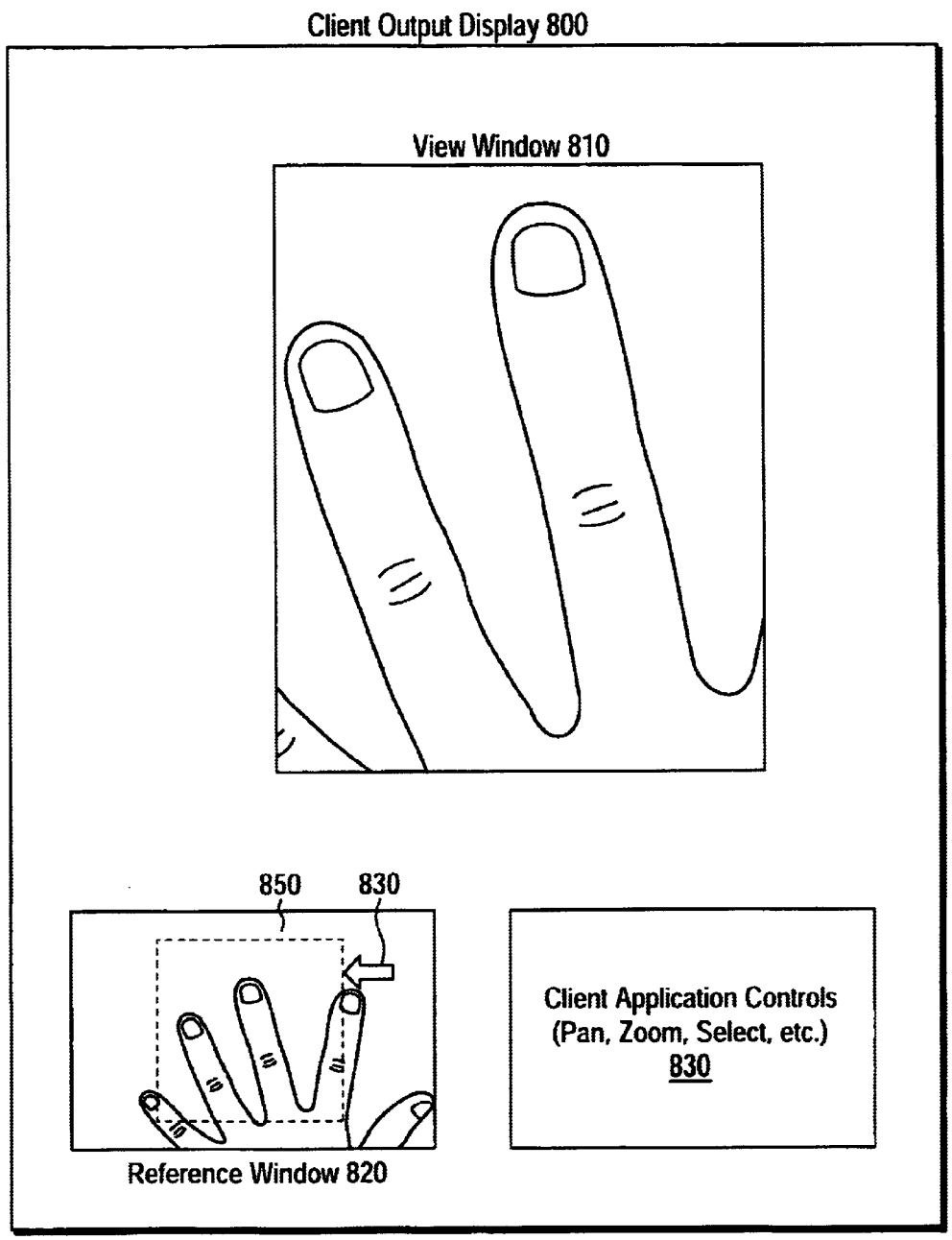

FIGS. 8a & 8b illustrate one embodiment of a client output display for implementing a medical imaging application using the dynamic transfer syntax of the present invention. For this embodiment, the client application (block 340, FIG. 3) is tailored for a medical application. Specifically, the client application permits a viewer, such as a doctor or other medical professional, to view large source images, such as X-rays, at various views and resolutions on a primary display area of the client output display 800, labeled view window 810 in FIG. 8a. For this embodiment, a small display window, entitled reference window 820, is displayed in the lower left corner of the client output display 800. The reference window 820 permits a user to view large portions of the image, at low resolution, for selection of sub-images within the larger source image. In one embodiment, the server transfers a low resolution full image view of the source image for display in the reference window 820. For example, if the source image is a 2K×2K image, and the reference window comprises 512×512 pixels, then the server transmits level two low-pass coefficients to represent the source image in the 512×512 reference window.

The general operation of the medical application deploying the dynamic transfer syntax system follows. An image in DICOM format is received from the image archive 112 of FIG. 1, or in alternative embodiments, an image is received directly from imaging equipment 105. The image is wavelet encoded (decomposition 120), and the resulting encoded image is stored within the server 140. In one embodiment for a medical application, the image is logged into an image database (not shown), accessible by a client 150, in order to select the image for viewing. For example, the images for a particular patient may be logged in a manner to associate the image with a medical record for the patient. When the client 150 accesses the patient's medical record, an indication of the image appears. In one embodiment, this indication may take the form of a thumbnail sketch of the image, (displayed in the reference window 820), along with identifying data such as a title (e.g., "Chest X-Ray) and date.

Using the AC 140 (FIG. 1), the client 150 requests the image for viewing. The request message includes an identifier of the image in the database. The server 140 responds by forwarding the request to an image service, which in turn, creates an instance of an image process specifically associated with the requested image and the requesting client. The image service returns information to the client 150 that enables the client to establish communications with the image process via a SC 144. This information may take the form, for example, of an host IP address and port number. The master client forwards this information to the client 150, which then establishes the SC 44 with the image process. Once the SC 44 is established, the image may be viewed.

In alternative embodiments, the image process may reside on a different server from the server on which the master server process and/or the image service resides. In such embodiments, the communication between components takes the form of remote procedure calls or other network communications mechanisms. Also, there may be multiple clients 150 accessing a single image instance, for example to enable geographically separated colleagues to collaborate in real time on a study or diagnosis. In such embodiments, the master server process and image service include functions that enable a client 150 to locate and connect to an existing image process.

The client application controls 830, shown in FIG. 8a, comprise the means to permit the client to select functions to view portions of the source image. In one embodiment, the client application controls 830 permits a user of the client system to pan the source image in virtual real-time. As shown in FIGS. 8a & 8b, the client application includes a cursor 830 that permits moving a select box 850 within the reference window 820. The select box 850 defines a region for the user to select a new view of the source image at a greater resolution. For example, by allowing the user to place the select box over a portion of the image in the reference window with a pre-defined zoom factor, user input is generated to execute a zoom operation. Also, by allowing the user to move the select box over a portion of the image in the reference window, user input to execute a virtual real time panning operation is generated. For the virtual real time panning operation, the area encompassed by the select box 850 is displayed on the view window 810 at a predetermined resolution in response to the movement of the select box 850. The operation is performed in "virtual real-time" because as the user moves the select box 850 in the reference window 820, the client/server, using the dynamic transfer syntax, displays that portion on the view window 810.

In one embodiment, the client application controls 830 also provides the functionality to zoom in on a portion of the source image identified by the select window 850. For this operation, the user, using the cursor 830, moves the select box 850 across the reference window 820 to select a desired portion of the source image. Once identified, the zoom command is executed, either through a pull down menu or keystroke, to select the portion of the source image to view in the view window 810. The pan and zoom operations are graphically illustrated in FIGS. 8a and 8b with the display in the reference window 820 of FIG. 8a of a selected portion of a source image, selected using the select box 850, and with the display of the selected portion of the source image shown in the view window 810 of FIG. 8b.

Computer System

Figure 9:
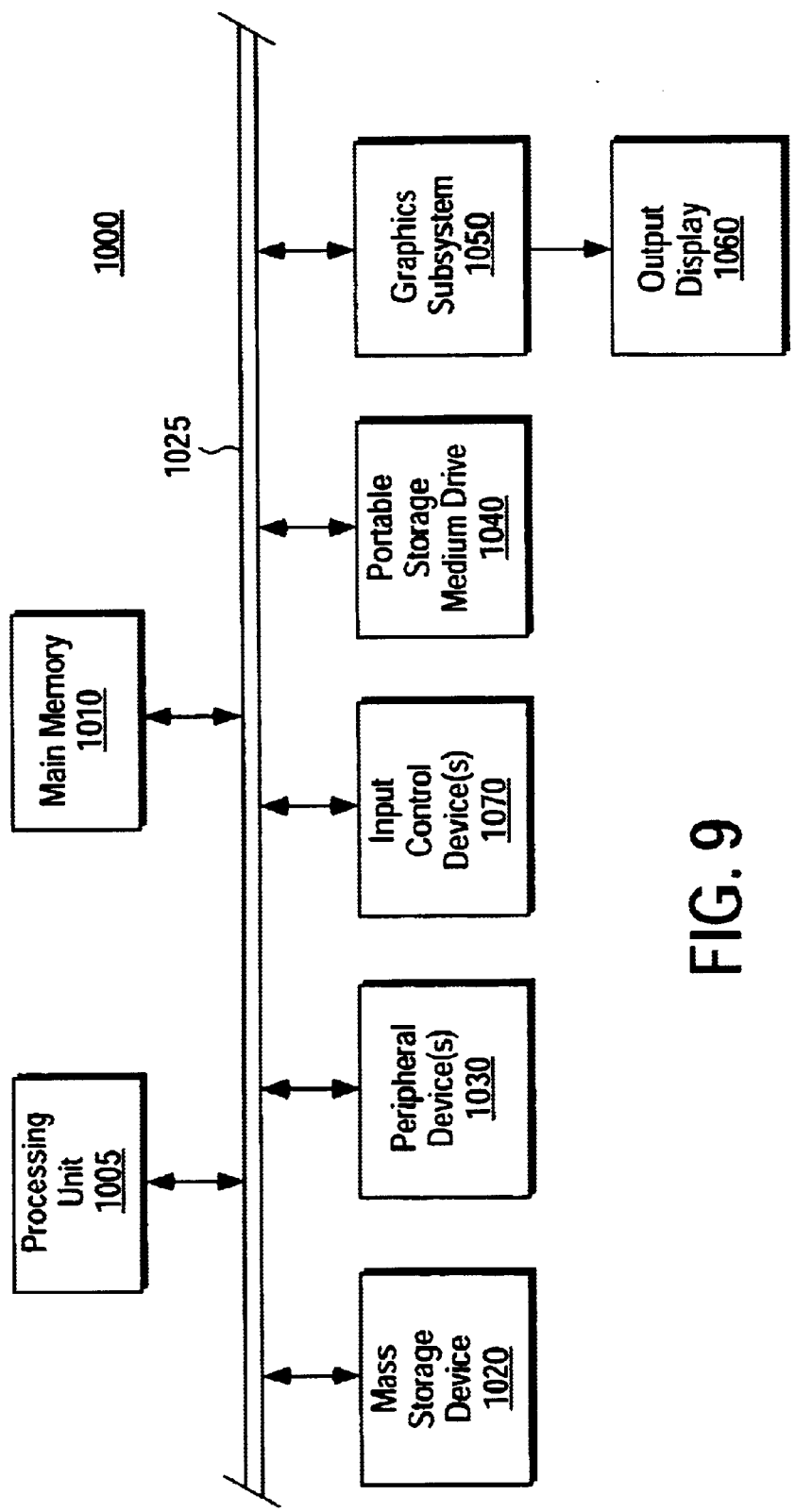
FIG. 9 illustrates a high level block diagram of a general purpose computer system in which the dynamic transfer syntax system of the present invention may be implemented.

FIG. 9 illustrates a high level block diagram of a general purpose computer system in which the dynamic transfer syntax system of the present invention may be implemented. A computer system 1000 contains a processor unit 1005, main memory 1010, and an interconnect bus 1025. The processor unit 1005 may contain a single microprocessor, or may contain a plurality of microprocessors for configuring the computer system 1000 as a multi-processor system. The main memory 1010 stores, in part, instructions and data for execution by the processor unit 1005. If the dynamic transfer syntax system of the present invention is wholly or partially implemented in software, the main memory 1010 stores the executable code when in operation. The main memory 1010 may include banks of dynamic random access memory (DRAM) as well as high speed cache memory.

The computer system 1000 further includes a mass storage device 1020, peripheral device(s) 1030, portable storage medium drive(s) 1040, input control device(s) 1070, a graphics subsystem 1050, and an output display 1060. For purposes of simplicity, all components in the computer system 1000 are shown in FIG. 9 as being connected via the bus 1025. However, the computer system 1000 may be connected through one or more data transport means. For example, the processor unit 1005 and the main memory 1010 may be connected via a local microprocessor bus, and the mass storage device 1020, peripheral device(s) 1030, portable storage medium drive(s) 1040, graphics subsystem 1050 may be connected via one or more input/output (I/O) busses. The mass storage device 1020, which may be implemented with a magnetic disk drive or an optical disk drive, is a non-volatile storage device for storing data and instructions for use by the processor unit 1005. In the software embodiment, the mass storage device 1020 stores the dynamic transfer syntax system software for loading to the main memory 1010.

The portable storage medium drive 1040 operates in conjunction with a portable non-volatile storage medium, such as a floppy disk or a compact disc read only memory (CD-ROM), to input and output data and code to and from the computer system 1000. In one embodiment, the dynamic transfer syntax system software is stored on such a portable medium, and is input to the computer system 1000 via the portable storage medium drive 1040. The peripheral device (s) 1030 may include any type of computer support device, such as an input/output (I/O) interface, to add additional functionality to the computer system 1000. For example, the peripheral device(s) 1030 may include a network interface card for interfacing the computer system 1000 to the network 160. For the software implementation, source images 110 and the hierarchical representation of the pyramidal data structure 130 may be input to the computer system 1000 via a portable storage medium or a network for processing by the dynamic transfer syntax system.

The input control device(s) 1070 provide a portion of the user interface for a user of the computer system 1000. The input control device(s) 1070 may include an alphanumeric keypad for inputting alphanumeric and other key information, a cursor control device, such as a mouse, a trackball, stylus, or cursor direction keys. In order to display textual and graphical information, the computer system 1000 contains the graphics subsystem 1050 and the output display 1060. The output display 1060 may include a cathode ray tube (CRT) display, a liquid crystal display (LCD), or a flat panel display. The graphics subsystem 1050 receives textual and graphical information, and processes the information for output to the output display 1060. The components contained in the computer system 1000 are those typically found in general purpose computer systems, and in fact, these components are intended to represent a broad category of such computer components that are well known in the art.

The dynamic transfer syntax techniques may be implemented in either hardware or software. For the software implementation, the dynamic transfer syntax system is software that includes a plurality of computer executable instructions for implementation on a general purpose computer system. Prior to loading into a general purpose computer system, the dynamic transfer syntax system software may reside as encoded information on a computer readable medium, such as a magnetic floppy disk, magnetic tape, and compact disc read only memory (CD-ROM). In one hardware implementation, the dynamic transfer syntax system may comprise a dedicated processor including processor instructions for performing the functions described herein.

Circuits may also be developed to perform the functions described herein.

Although the present invention has been described in terms of specific exemplary embodiments, it will be appreciated that various modifications and alterations might be made by those skilled in the art without departing from the spirit and scope of the invention.

What is claimed is:

1. A method for transferring data from a server to at least one client, said method comprising the steps of:

transforming source data into a hierarchical representation using a wavelet transform with fixed point kernels, said hierarchical representation comprising a plurality of levels of essentially non-redundant data, wherein a level of said hierarchical representation comprises transform data sufficient to reconstruct said source data at a resolution corresponding to said level;

requesting, from a client to a server, transform data from a level of said hierarchical representation necessary to reconstruct at least a portion of said source data;

transferring, from said server to said client, said transform data from said hierarchical representation requested by said client; and re-constructing, at said client, said portion of said source image for display at said client with said transform data.

2. The method as set forth in claim 1, further comprising the steps of:

requesting, from said client to said server, transform data from said hierarchical representation necessary to reconstruct a new portion of said source data;

transferring, from said server to said client, additional transform data from a level of said hierarchical representation, corresponding to said new portion of said source data, down one or more lower levels of said hierarchical representation to said level previously transferred; and reconstructing said new portion of said source data with said additional transform data and said transform data originally transferred, whereby only incremental transform data necessary to construct said new portion of said source data at said client is transferred from said server to said client.

3. The method as set forth in claim 1, wherein:

the step of transforming said source data into a hierarchical representation comprises the step of utilizing said wavelet transform to generate a plurality of low pass coefficients and a plurality of high pass coefficients;

the step of requesting data from said hierarchical representation comprises the step of transferring coefficient coordinates to identify coefficients sufficient to re-construct said portion of said source image; and the step of re-constructing said portion of said source image comprises the step of transforming said coefficients to generate said portion of said source image.

4. The method as set forth in claim 3, wherein the step of utilizing said wavelet transform to generate a plurality of low pass coefficients and a plurality of high pass coefficients comprises the step of generating low pass coefficients for each level of said hierarchical representation, so as to aggregate sufficient information to render a viewable display of said source image at a resolution corresponding to said level.

5. The method as set forth in claim 3, wherein the step of requesting, from said client to said server, transform data comprises the step of transferring O(N) coefficients to represent "N" pixels for display at said client, wherein "N" comprises an integer value.

6. The method as set forth in claim 1, wherein the step of transforming said source data into a hierarchical representation comprises the step of executing a finite impulse response function to generate said transform data.

7. The method as set forth in claim 1, wherein the step of transforming said source data into a hierarchical representation comprises the step of preserving geometry between said source data and said transform data, so that any portion of said source data is identifiable from a portion of said transform data.

8. A method for transferring data images from a server to at least one client, said method comprising the steps of:

generating a hierarchical representation of a source image using a wavelet transform with fixed point kernels, said hierarchical representation comprising a plurality of levels of essentially non-redundant data, wherein a level of said hierarchical representation comprises data sufficient to reconstruct said source image at a resolution corresponding to said level;

transferring, from a server to a client, at least a portion of data from a level of said hierarchical representation of said source image at a first resolution, said first resolution being less than full resolution of said source image;

requesting, from said client to said server, data from said hierarchical representation, additional to said portion of data transferred, necessary to reconstruct said source image at pixel coordinates for said source image; and transferring, from said server to said client, said additional data requested to display at said client said source image at said pixel coordinates, whereby only data of said hierarchical representation necessary to construct said source image at a pre-determined resolution at said client is transferred from said server to said client.

9. The method as set forth in claim 8, wherein:

the step of generating a hierarchical representation of a source image comprises the step of generating said wavelet decomposition for each level of said hierarchical representation comprising low pass coefficients and a plurality of high pass coefficients;

the step of transferring, from a server to a client, data from a level of said hierarchical representation comprises the step of transferring low pass coefficients corresponding to a level for said first resolution; and the step of requesting, from said client to said server, additional data, comprises the step of transferring additional high pass coefficients necessary to construct said source image at said pixel coordinates.

10. The method as set forth in claim 8, wherein the step of requesting, from said client to said server, additional data, comprises the step of transferring O(N) coefficients to present "N" pixels for said pixel coordinates, wherein "N" comprises an integer value.

11. The method as set forth in claim 8, wherein:

the step of transferring, from a server to a client, at least a portion of data comprises the step of transferring a portion of said source image at a zoom resolution greater than a resolution capable of display at said client; and the step of requesting, from said client to said server, data from said hierarchical representation comprises the step of requesting pixel coordinates to pan said source image at a resolution at least as great as said zoom resolution.

12. The method as set forth in claim 8, wherein:

the step of transferring, from a server to a client, at least a portion of data comprises the step of transferring said source image at said first resolution; and the step of requesting, from said client to said server, data from said hierarchical representation comprises the step of requesting pixel coordinates at a second resolution, greater than said first resolution.

13. A system comprising:

a server for storing transform data as a hierarchical representation, said transform data generated from source data using a wavelet transform with fixed point kernels, said hierarchical representation comprising a plurality of levels of essentially non-redundant data, wherein a level of said hierarchical representation comprises transform data sufficient to reconstruct said source data at a resolution corresponding to said level;

at least one client, coupled to communicate with said server, said client requesting to said server transform data from a level of said hierarchical representation necessary to reconstruct at least a portion of said source data;

said server for transferring to a client said transform data from said hierarchical representation upon request by said client; and said client for re-constructing, at said client, said portion of said source image for display at said client with said transform data.

14. The system as set forth in claim 13, wherein:

said client further comprises software for requesting, to said server, transform data from said hierarchical representation necessary to reconstruct a new portion of said source data;

said server further comprises software for transferring, to said client, additional transform data from a level of said hierarchical representation, corresponding to said new portion of said source data, down one or more lower levels of said hierarchical representation to said level previously transferred; and said client further comprises software for reconstructing said new portion of said source data with said additional transform data and said transform data originally transferred, whereby only incremental transform data necessary to construct said new portion of said source data at said client is transferred from said server to said client.

15. A computer readable medium comprising a plurality of instructions, which when executed by a computer, cause the computer to perform the steps of:

transforming source data into a hierarchical representation using a wavelet transform with integer kernels, said hierarchical representation comprising a plurality of levels of essentially non-redundant data, wherein a level of said hierarchical representation comprises transform data sufficient to reconstruct said source data at a resolution corresponding to said level;

requesting, from a client to a server, transform data from a level of said hierarchical representation necessary to reconstruct at least a portion of said source data;

transferring, from said server to said client, said transform data from said hierarchical representation requested by said client; and re-constructing, at said client, said portion of said source image for display at said client with said transform data.

16. The computer readable medium as set forth in claim 15, further comprising the steps of:
- requesting, from said client to said server, transform data from said hierarchical representation necessary to reconstruct a new portion of said source data;
- transferring, from said server to said client, additional transform data from a level of said hierarchical representation, corresponding to said new portion of said source data, down one or more lower levels of said hierarchical representation to said level previously transferred; and
- reconstructing said new portion of said source data with said additional transform data and said transform data originally transferred, whereby only incremental transform data necessary to construct said new portion of said source data at said client is transferred from said server to said client.

17. The computer readable medium as set forth in claim 15, wherein:
- the step of transforming said source data into a hierarchical representation comprises the step of utilizing said wavelet transform to generate a plurality of low pass coefficients and a plurality of high pass coefficients;
- the step of requesting data from said hierarchical representation comprises the step of transferring coefficient coordinates to identify coefficients sufficient to re-construct said portion of said source image; and
- the step of re-constructing said portion of said source image comprises the step of transforming said coefficients to generate said portion of said source image.

18. The computer readable medium as set forth in claim 17, wherein the step of utilizing said wavelet transform to generate a plurality of low pass coefficients and a plurality of high pass coefficients comprises the step of generating low pass coefficients for each level of said hierarchical representation, so as to aggregate sufficient information to render a viewable display of said source image at a resolution corresponding to said level.

19. The computer readable medium as set forth in claim 17, wherein the step of requesting, from said client to said server, transform data comprises the step of transferring O(N) coefficients to represent "N" pixels for display at said client, wherein "N" comprises an integer value.

20. The computer readable medium as set forth in claim 15, wherein the step of transforming said source data into a hierarchical representation comprises the step of executing a finite impulse response function to generate said transform data.

21. The computer readable medium as set forth in claim 15, wherein the step of transforming said source data into a hierarchical representation comprises the step of preserving geometry between said source data and said transform data, so that any portion of said source data is identifiable from a portion of said transform data.

* * * * *